(12) United States Patent
Zens

(10) Patent No.: US 10,241,165 B2
(45) Date of Patent: Mar. 26, 2019

(54) INDUCTIVE COUPLING IN MULTIPLE RESONANCE CIRCUITS IN A NUCLEAR MAGNETIC RESONANCE PROBE AND METHODS OF USE

(71) Applicant: JEOL LTD., Tokyo (JP)

(72) Inventor: Albert Zens, Peabody, MA (US)

(73) Assignee: JEOL LTD, Tokyo (JP)

( * ) Notice: Subject to any disclaimer, the term of this patent is extended or adjusted under 35 U.S.C. 154(b) by 0 days.

(21) Appl. No.: 15/575,813

(22) PCT Filed: Mar. 14, 2017

(86) PCT No.: PCT/JP2017/010178
§ 371 (c)(1),
(2) Date: Nov. 20, 2017

(87) PCT Pub. No.: WO2017/159676
PCT Pub. Date: Sep. 21, 2017

(65) Prior Publication Data
US 2018/0267118 A1 Sep. 20, 2018

Related U.S. Application Data

(60) Provisional application No. 62/307,570, filed on Mar. 14, 2016.

(51) Int. Cl.
*G01V 3/00* (2006.01)
*G01R 33/36* (2006.01)
*A61B 5/055* (2006.01)

(52) U.S. Cl.
CPC ..... *G01R 33/3642* (2013.01); *G01R 33/3635* (2013.01); *A61B 5/055* (2013.01)

(58) Field of Classification Search
CPC .................................................. G01R 33/3635
(Continued)

(56) References Cited

U.S. PATENT DOCUMENTS 5,003,265 A * 3/1991 Leussler .......... G01R 33/34053
324/318
5,243,289 A 9/1993 Blum
(Continued)

FOREIGN PATENT DOCUMENTS

| WO | WO2010/018535 | 2/2010 |
| WO | WO2013/108142 | 7/2013 |
| WO | WO2016/166609 | 10/2016 |

OTHER PUBLICATIONS

PCT International Search Report, PCT/JP2017/010178, dated Oct. 16, 2017, 17 pages (ISA 210, ISA 220, ISA 237).
(Continued)

*Primary Examiner* — Louis Arana
(74) *Attorney, Agent, or Firm* — SCI-Law Strategies, PC

(57) ABSTRACT

In various embodiments of the invention, inductive coupling can be to a secondary coil rather than a primary coil in order to optimize the topology of the NMR probe. In addition, by coupling to a secondary coil using a detection coil located below the lower insulator the RF homogeneity and signal to noise can be improved together with the NMR probe topology. By effecting inductive coupling to an inductor in a multiple resonance circuit, rather than to the sample inductor parameters associated with the NMR, probe construction can be arranged to increase RF homogeneity and signal to noise, while reducing space utilization constraints. In various embodiments of the invention, the primary mode in a secondary coil can be split into two modes with a resonator with inductive coupling to the secondary coil.

17 Claims, 23 Drawing Sheets

(58) Field of Classification Search
USPC .................................................. 324/322, 318
See application file for complete search history.

(56) References Cited

U.S. PATENT DOCUMENTS

| | | | |
|---|---|---|---|
| 5,483,163 A | 1/1996 | Wen | |
| 5,585,721 A * | 12/1996 | Datsikas | G01R 33/34046 |
| | | | 324/318 |
| 2001/0033165 A1 | 10/2001 | Tomanek | |
| 2009/0256569 A1 | 10/2009 | Hanen | |
| 2011/0025326 A1 | 2/2011 | Zens | |
| 2014/0057792 A1 | 2/2014 | Brey | |
| 2018/0252783 A1* | 9/2018 | Jones | G01R 33/3657 |
| 2018/0321339 A1* | 11/2018 | Yang | G01R 33/34084 |

OTHER PUBLICATIONS

PCT Rule 43bis.1, International Search Report, PCT/IB2016/000730, dated Sep. 11, 2016, 15 pages.

Bowyer P., et al., Using Magnetic Coupling to Implement 1H, 19F, 130 experiments in routine high resolution NMR probes, J Mag Reson., 261 (2015) 190-198.

Van Hecke, P., et al., Double Tuned Resonator Designs for NMR Spectroscopy, , J Mag Reson., 84 (1989) 170-176.

Kuhns, P., et al., Inductive Coupling and Tuning in NMR Probes; Applications, J Mag Reson., 78 (1988) 69-76.

EPO Communication Art 94(3) EPC for Application 17719932.0, dated Jan. 14, 2019, 8 pages.

* cited by examiner

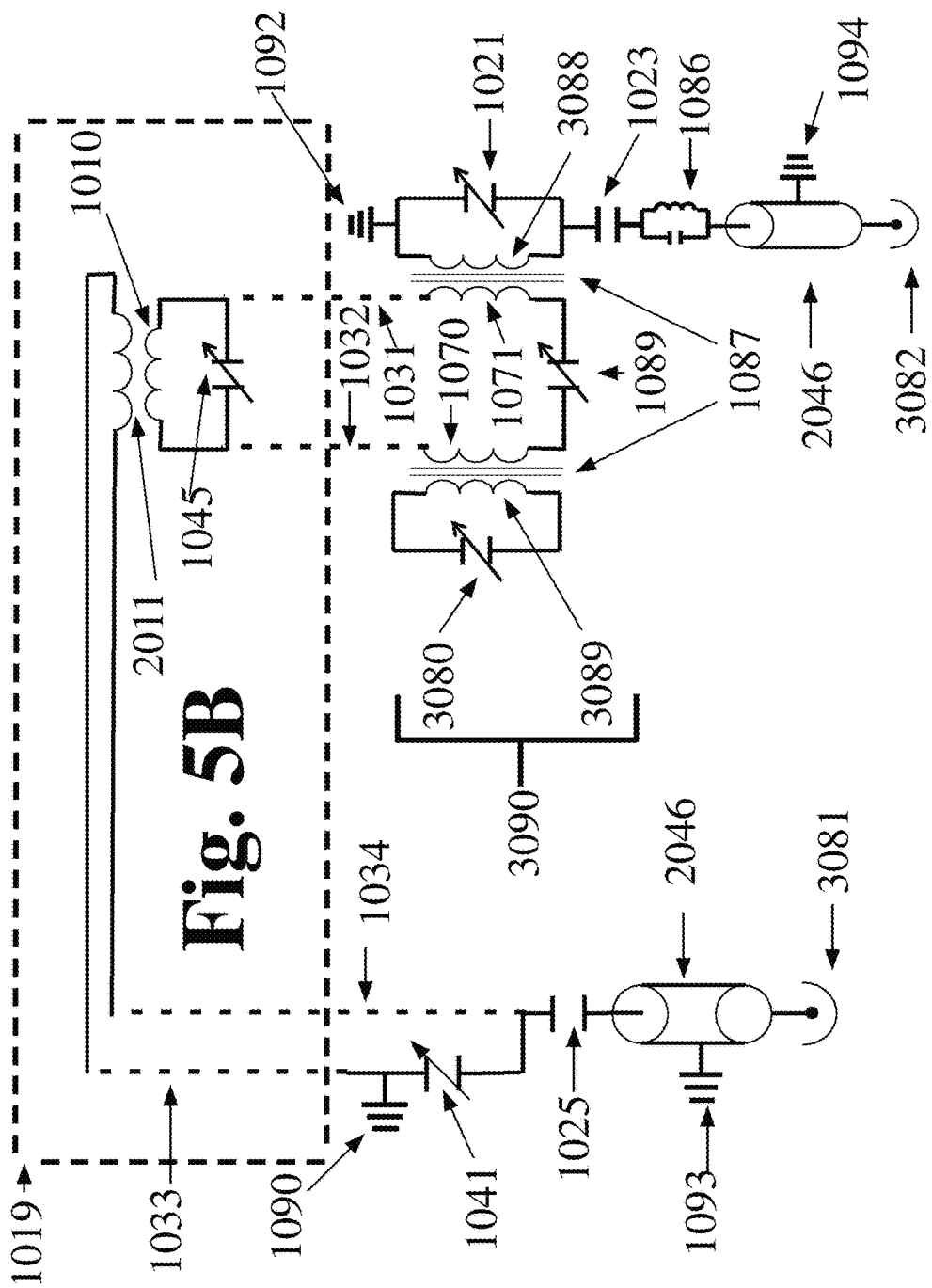

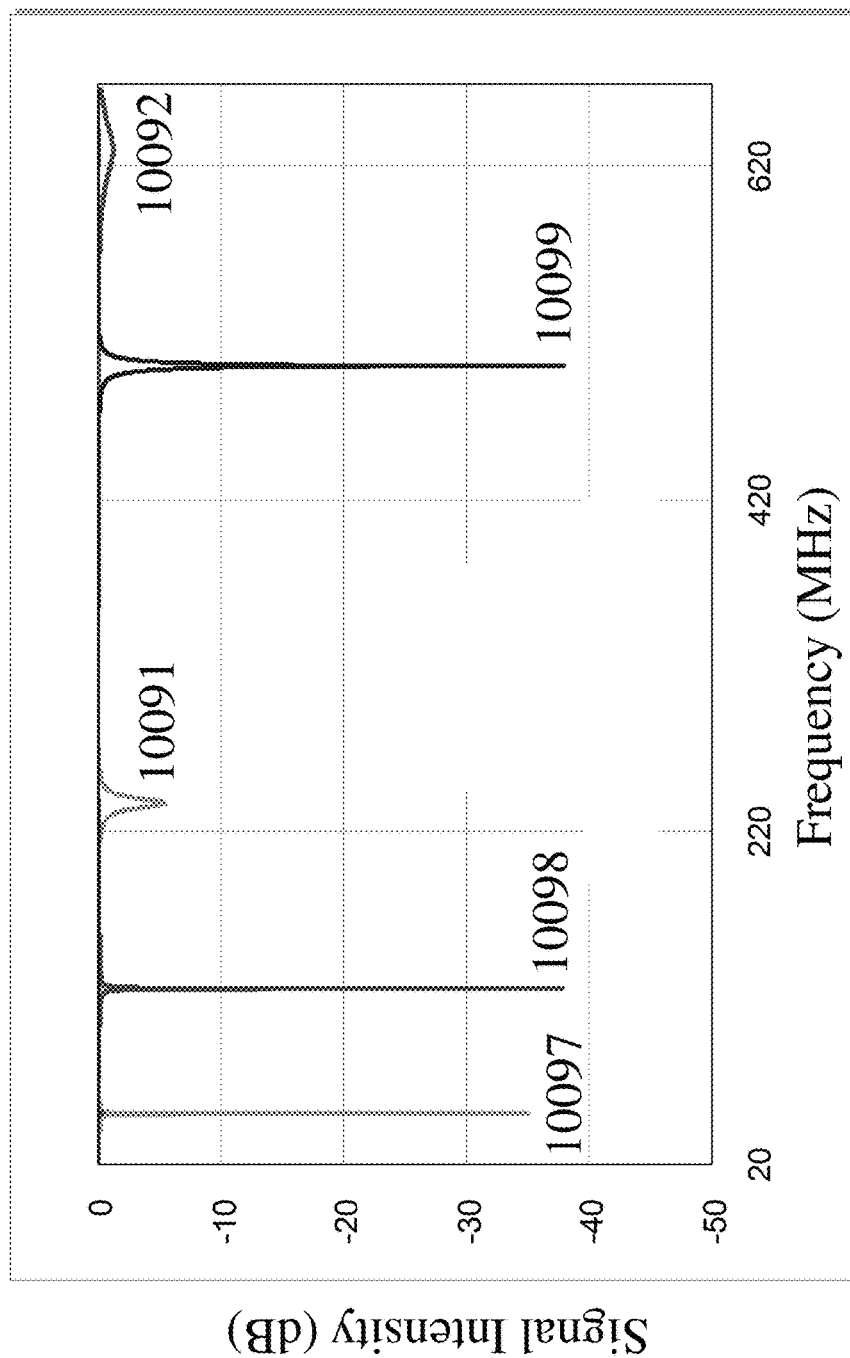

INDUCTIVE COUPLING IN MULTIPLE RESONANCE CIRCUITS IN A NUCLEAR MAGNETIC RESONANCE PROBE AND METHODS OF USE

FIELD OF THE INVENTION

The present invention relates to methods and NMR probe devices using multiple resonance circuits in magnetic resonance. In this invention coupling coils and resonators are coupled to a secondary coil rather than coupling to the parent coil or sample coil in order to improve the space utilization within the probe, the RF homogeneity of the parent coil, and the signal to noise of the circuit.

BACKGROUND OF THE INVENTION

Structural elucidation of a compound, whether a synthesis product or an extract from a natural source generally requires a number of analytical techniques. Infrared spectroscopy, mass spectrometry, and nuclear magnetic resonance (NMR) spectroscopy can provide extensive chemical information. NMR can provide structural information and also information on both intermolecular and intramolecular dynamics. Applications of NMR range from determination of three-dimensional structures of large proteins to the analysis of very small amounts of products from combinatorial syntheses. Furthermore, NMR is a nondestructive analytical method.

NMR probes typically have an inner coil for irradiation and detection of a first nuclear species, and a second larger coil coaxial with the inner coil for irradiation and or detection of one or more other nuclear species. The two coils can be oriented 90° with respect to each other to minimize coupling between the two coils. It should also be recognized that all of the inductors in the probe circuits should have minimal coupling (k<approximately 0.03) between them in order to reduce or eliminate cross talk between these elements unless the magnetic coupling is intended. Capacitive coupling has can be used to form multiply-tuned NMR probes for $^1H$-$^2H$, $^{13}C$-$^{15}N$ and $^1H$-$^{19}F$. Recently it has been shown by Zens in U.S. provisional patent application No. 62/148,137 entitled "NMR Analysis using a Dual Probe for HFC Measurements", filed Apr. 15, 2015, that magnetic coupling can also be used to improve these multiple resonance circuits, which is explicitly incorporated by reference in its entirety.

The sample region can contain or all of the following: 1) multiple sample coils, 2) magnetic coupling loops, 3) coupling resonators, 4) variable tuning capacitors, 5) pulse field gradients, 6) Faraday shields, 7) loop gap shields and other components related to the performance and function of the probe that those skilled in the art of probe fabrication would recognize.

SUMMARY OF THE INVENTION

A problem in the NMR field is that prior art probe devices do not provide sufficient space above the lower insulator for all the components that surround the sample. These include 1) multiple sample coils, 2) magnetic coupling loops, 3) coupling resonators, 4) variable tuning capacitors, 5) pulse field gradients, 6) Faraday shields, 7) loop gap shields and other components that are known to those skilled in the art of probe design. The magnetic coupling loops, coupling resonators, variable tuning capacitors, pulse field gradients, Faraday shields and loop gap shields can all be detrimental to the performance of the probe in some manner. The $B_0$ homogeneity can be impacted by the susceptibility of these objects, The Q of the sample coil(s) can be diminished. The RF homogeneity of the sample coils can be impacted by the presence of additional metallic objects and the presence magnetic coupling loops or resonators that couple to the sample inductor. All of the above, shields, coupling loops, variable capacitors, resonators, pulse field gradients etc., can dilute the signal to noise of the NMR experiment even if only in a minor manner. From the above it is clear that fewer objects in the sample region of the NMR probe is a condition that should be strived for in the development and improvement of magnetic resonance (NMR) detection devices.

In an embodiment of the invention, inductive coupling to a secondary coil can be incorporated in a region away from the sample coil and thereby allow for improved space utilization in the NMR probe in the sample region, while allowing for improved magnetic field ($B_0$) homogeneity, RF homogeneity and increased signal to noise. In various embodiments of the present invention, inductive coupling of a coupling coil positioned outside the region to at least one secondary coil rather than the primary coil can eliminate adverse inhomogeneity effects on the sample inductor thereby allowing parameters associated with the NMR probe construction to be arranged to increase magnetic field ($B_0$) homogeneity, RF homogeneity and increase signal to noise, while reducing space utilization constraints in the region.

In an alternative embodiment of the invention, inductive coupling to a secondary coil can be incorporated below the lower insulator and thereby allow for improved space utilization in the NMR probe above the lower insulator, while allowing for improved magnetic field ($B_0$) homogeneity, RF homogeneity and increased signal to noise. In various alternative embodiments of the present invention, separating components below the lower insulator with inductive coupling to at least one secondary coil rather than the primary coil can eliminate adverse inhomogeneity effects on the sample inductor thereby allowing parameters associated with the NMR probe construction to be arranged to increase magnetic field ($B_0$) homogeneity, RF homogeneity and increase signal to noise, while reducing space utilization constraints.

In a further embodiment of the invention, a resonator distal to the sample coil can be coupled to one of the secondary coils in order to split the resonance into two modes allowing for improved space utilization in the NMR probe in the sample region, while allowing for improved magnetic field ($B_0$) homogeneity, RF homogeneity and increased signal to noise.

In an additional embodiment of the invention, a resonator located below the lower insulator, where the sample coil is located above the lower insulator can be coupled to one of the secondary coils in order to split the resonance into two modes allowing for improved space utilization in the NMR probe in the sample region, while allowing for improved magnetic field ($B_0$) homogeneity, RF homogeneity and increased signal to noise.

BRIEF DESCRIPTION OF THE DRAWINGS

This invention is described with respect to specific embodiments thereof. Additional aspects can be appreciated from the Figures in which:

FIG. 5B is a schematic diagram showing a sample coil and a coupling loop located in the sample resonator region for a split resonance circuit with the inductive coupling circuit(s) outside the sample resonator in a manner similar to FIG. 5A, according to an embodiment of the present invention;

FIG. 10C is an S(1,1), S(2,2), S(3,3) simulation showing the signal intensity versus the frequency for three resonances $^{13}C$ 10097, $^1H$ 10098 and $^{15}N$ 10099 based on the circuit shown in FIG. 10A and FIG. 10B, according to an embodiment of the present invention.

DETAILED DESCRIPTION OF THE INVENTION

Definitions

Figure 1A:
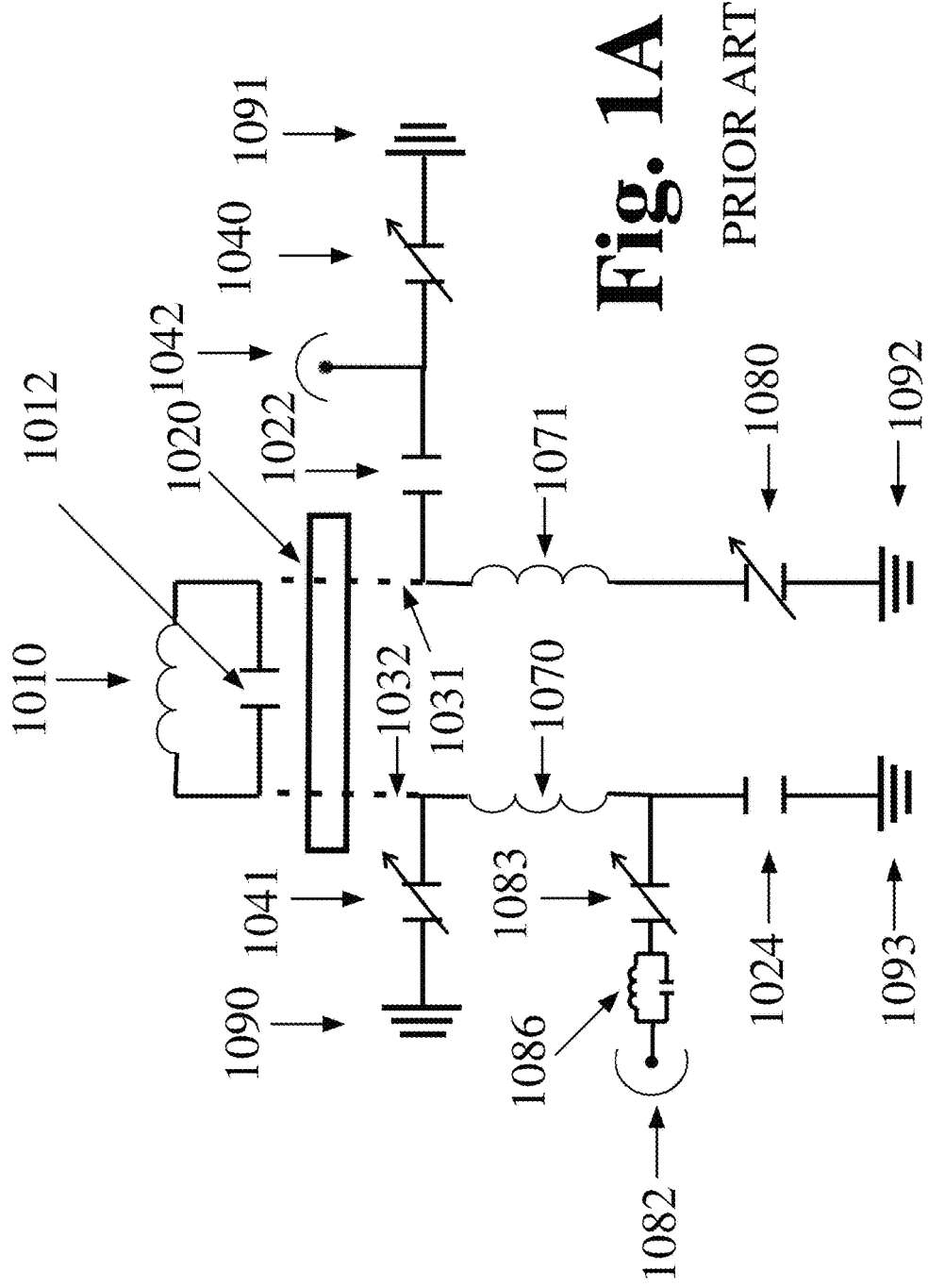
FIG. 1A is a schematic diagram of a double tuned circuit for a $^1H/^2H$ with a lower insulator.

The transitional term 'comprising' is synonymous with 'including', 'containing', or 'characterized by', is inclusive or open-ended and does not exclude additional, unrecited elements or method steps.

The transitional phrase 'consisting of' excludes any element, step, or ingredient not specified in the claim, but does not exclude additional components or steps that are unrelated to the invention such as impurities ordinarily associated with a composition.

The transitional phrase 'consisting essentially of' limits the scope of a claim to the specified materials or steps and those that do not materially affect the basic and novel characteristic(s) of the claimed invention.

The word 'deployed' means attached, affixed, adhered, inserted, located or otherwise associated.

A 'cell' means a vessel used to contain one or more of a homogeneous or heterogeneous liquid, gas or solid sample.

A 'screen' means two or more connected filaments, a mesh, a grid or a sheet. In various embodiments of the invention, a screen includes three or more connected filaments where at least one filament is approximately orthogonal to one other filament. A screen thickness is greater than approximately 20 micrometer and less than approximately one centimeter, where approximately is ±twenty (20) percent. A metallic screen is a screen where the filaments, mesh, grid or sheet block magnetic coupling or RF fields.

Coupling to various coils of different sizes and functions can be used to optimize the circuit. A sample coil, a coupling coil, a lock coil, a splitting coil and a detector coil can be Helmholtz coils. A sample coil, a coupling coil, a lock coil, a splitting resonator and a detector coil can be a solenoid coil.

A 'shunt' means a translation stage that allows the inductive coil and or the inductive coil circuit to be moved relative to another inductive coil.

A 'filament' means a wire with a diameter greater than approximately 20 micrometer and less than approximately one centimeter, where approximately is ±twenty (20) percent.

The word mode means a resonance in the circuit. The number of modes in a circuit cannot exceed the number of inductors.

The words or phrases 'coupling', 'coupling modes', 'detecting' or 'detecting modes' mean matching the modes in a circuit such that the critical coupling constant is achieved. The critical coupling is necessary for matching the resistance to a fifty (50) Ohm coax. In various embodiments of the invention, the resistance can be matched to other resistance coax. In an embodiment of the invention, the resistance can be coupled to seventy five (75) Ohm coax. In various embodiments of the invention, seventy seven (77) Ohm coax gives minimum loss.

The phrases 'parent coil', 'primary coil', 'tertiary coil' or 'sample coil' means the inductor constructed to observe the sample resonance.

The phrase 'tertiary coil' means the inductor, constructed to enable, observe or irradiate a second nuclear species.

The phrase 'sample resonator' refers to an inductive coil and capacitor. A sample resonator can be used for detecting the fluctuating signal that is in resonance with a signal from a sample. In circumstances where there is no lower threshold, a first distance is defined between the sample resonator and the one or more inductive coupling loops. A resonant circuit is an electric circuit which has oscillating currents which are stored as energy and the impedance of the capacitor and inductor are near zero. The only losses in the circuit are from the pure resistive parts of the components, the inductor L and the capacitor C. Inductive coupling is the near field wireless transmission of electrical energy between two magnetically coupled coils.

A splitting resonator can be used to split a signal. The splitting resonator can be used to split the primary resonance into at least two signals. The splitting resonator can be used to split for example $^{13}C/^{27}Al$, $^{1}H/^{19}F$, $^{27}Al/^{65}Cu$, $^{17}O/^{63}Cu$, and $^{63}Cu/^{65}Cu$.

The word 'susceptibility' refers to the magnetic susceptibility of the materials used to construct the probe to preserve the $B_0$ homogeneity of the magnet in the sample region. Here "Zero Susceptibility" means very low volume susceptibility.

The phrase the 'inductive coupling loop' means an inductive coupling coil used to match a mode to fifty (50) ohm coax.

The phrase 'multiply tuned resonance circuit' means two (2) or more tuned circuits. In an embodiment of the invention, a triply tuned circuit consists of for example $^{13}C$, $^{2}H$ and $^{15}N$ tuned circuits. In an alternative embodiment of the invention, a triply tuned circuit consists of for example $^{13}C$, $^{1}H$ and $^{15}N$ tuned circuits.

The phrase 'lower insulator' means a partition between the region that houses the primary circuit and the area outside of the sample coil region. The tertiary coils can be located in the same region as the primary circuit. The secondary circuits are located outside the sample coil region. In various embodiments of the invention, some NMR probes, i.e. solids probes, do not use a formal lower insulator partition.

The phrase 'sample resonator' means an area of a NMR probe that houses the primary circuit.

The distance between the sample coil and either the one or more secondary inductor coils, inductive coupling loops, means the approximate distance between the sample coil and the closest of the one or more inductive coupling circuits between approximately $10^{-4}$ m and approximately $10^{-1}$ m, where approximate means ±ten (10) percent.

The phrase 'Circuit Fill Factor (CFF)' means for a specific mode, k, the definition of CFF referred to reference inductor is $$CFF_{k,a} = \frac{L_a i_a^2}{\sum_{j=1}^{N} L_j i_j^2},$$

where i is the current in the inductor, the j indices identify specific inductors, and it is implicit that the current values are for the kth mode. It is clear that this definition does not accommodate the presence of mutual inductance. From the definition of CFF it is clear that having more inductors in the circuit dilutes the S/N of the multiply tuned probe circuit. For probe circuits with multiple ground points there exist the question of what is the common ground point. If the ground points are not at the same potential as the common ground point then each ground point is essentially and inductor to that common ground point and hence the potential to dilute the CFF of the circuit.

A metal comprises one or more elements consisting of lithium, beryllium, boron, carbon, nitrogen, oxygen, sodium, magnesium, aluminum, silicon, phosphorous, sulfur, potassium, calcium, scandium, titanium, vanadium, chromium, manganese, iron, cobalt, nickel, copper, zinc, gallium, germanium, arsenic, selenium, rubidium, strontium, yttrium, zirconium, niobium, molybdenum, technetium, ruthenium, rhodium, palladium, silver, cadmium, indium, tin, antimony, tellurium, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, thallium, lead, bismuth, polonium, francium and radium.

NMR generally uses induction to detect the oscillating magnetic moment from nuclei precessing in a magnetic field. Because the signal from these precessing nuclei is inherently weak research efforts have been focused on improving the signal to noise ratio obtained in NMR experiments. There are two general ways to increase the signal to noise ratio. One way is to increase the size of the magnetic moment by induced polarization. The other way is to decrease the noise by cooling the coils and electronics used to detect the signal. In the last 20 years cooling the coils has been the major focus of the research. For example, to provide improved sensitivity the electronics for signal detection can be cryo-cooled. In contrast, the signal to noise of the RF homogeneity of the parent coil can be degraded by magnetic coupling to the coil with even small k (coupling constant) values.

An NMR probe includes a complex array of field shimming or field improving devices to correct for magnetic field in-homogeneities. The probe can be a removable cylinder which contains: the sample tube holder and air spinner outlets; the radiofrequency coils for signal detection, spin irradiation, and locking of the magnetic field; the electronics, Dewar, gas inlets and outlets for cooling and heating of the sample; tuning coils for fine adjustments of the magnetic field, and coils for producing precise field gradients. For the most common nuclei, the magnetic moments are: $^1$H $\mu=2.7927$, $^2$H $\mu=0.8574$, $^{19}$F $\mu=2.6273$, $^{31}$P $\mu=1.1305$ & $^{13}$C $\mu=0.7022$. These moments are in nuclear magnetons, which are $5.05078\times10-27$ JT. The energy difference between two spin states is less than 0.1 cal/mole. The spins in the NMR experiment are detected by a resonator which in all cases detects the fluctuating signal with a circuit that is in resonance with the signal from the sample. That is, the circuit contains an inductor and capacitor which resonates at the Larmor (resonance frequency) frequency of the spins in the sample. The inductor usually encloses the NMR sample in a manner which closely approximates the sample volume. The signal from the resonator must be matched to a transmission line so that the excitation and detection of the signal can be accomplished with minimal loss. NMR Resonators can be designed in many shapes and forms. From simple solenoids to complex built in capacitance coil arrays. Often more than one spin type or nucleus is excited or detected during the course of an experiment. Multiple coils are used to accomplish this and the region around the sample can become space intensive in terms of the number of objects required to undertake the signal detection in the NMR experiment. Due to space considerations the sample coil surrounding the sample is often resonated such that it has multiple modes. However, the number of modes cannot exceed the number of inductors. The practice of employing multiple resonating sample coils helps reduce the number of resonators in the sample region of the NMR probe. For a typical multiple resonance probe that requires a lock resonance and three other resonant frequencies for the NMR experiment, this reduces the number of coils in the sample region from four to two. However, this reduction in the number of resonators doesn't come without a loss in signal to noise. Accordingly, circuit efficiency remains very important. The capacitive double resonance circuit shown in FIG. 1A has additional resonances in the circuit which originate from the fact that the inductors don't have a common ground point in the circuit. These additional resonances reduce the circuit fill factor.

An NMR probe can include a sample, a sample detection coil(s) and associated circuitry, a support for the sample detection coil(s), a pulsed field gradient, a shield, one or more coupling coils and associated circuitry, supports for the one or more coupling coils and inductors, capacitors and variable capacitors. A perturbation of the magnetic field or the flux generated by the sample coil will reduce the signal to noise. Accordingly, minimizing the components in the sample region of the NMR probe can reduce perturbations of the magnetic field ($B_0$), the RF homogeneity and accordingly increase the signal to noise.

FIG. 1A shows a double tuned circuit for a $^1$H/$^2$H resonance, with a sample inductor 1010, sample capacitor 1012, positioned above the lower insulator, 1020. The resonator lead #1 1031, and resonator lead #2, 1032, pass through the lower insulator, 1020 and connect the sample inductor, 1010 to inductor #1, 1070, and inductor #2, 1071. In various embodiments of the invention, the length of the resonator lead #1, 1031, and resonator lead #2, 1032 are not necessarily the same. Below the lower insulator, 1020 are located a fixed tune capacitor, 1022, a tune variable capacitor, 1041, a match variable capacitor, 1040, a $^1$H fifty (50) Ohm port, 1042, a inductor #1, 1070, a inductor #2, 1071, a match variable capacitor, 1083, a tune variable capacitor, 1080, a high frequency block, 1086, a $^2$H fifty (50) Ohm port, 1082, a tune capacitor, 1024, ground (#1), 1090, ground (#2), 1091, ground (#3), 1092 and ground (#4) 1093. The high frequency block, 1086 comprises an inductor and a capacitor in parallel where the resonator blocks high frequencies. The choice of the high frequency block is made so as not to overlap with the primary resonance frequency.

Figure 1B:
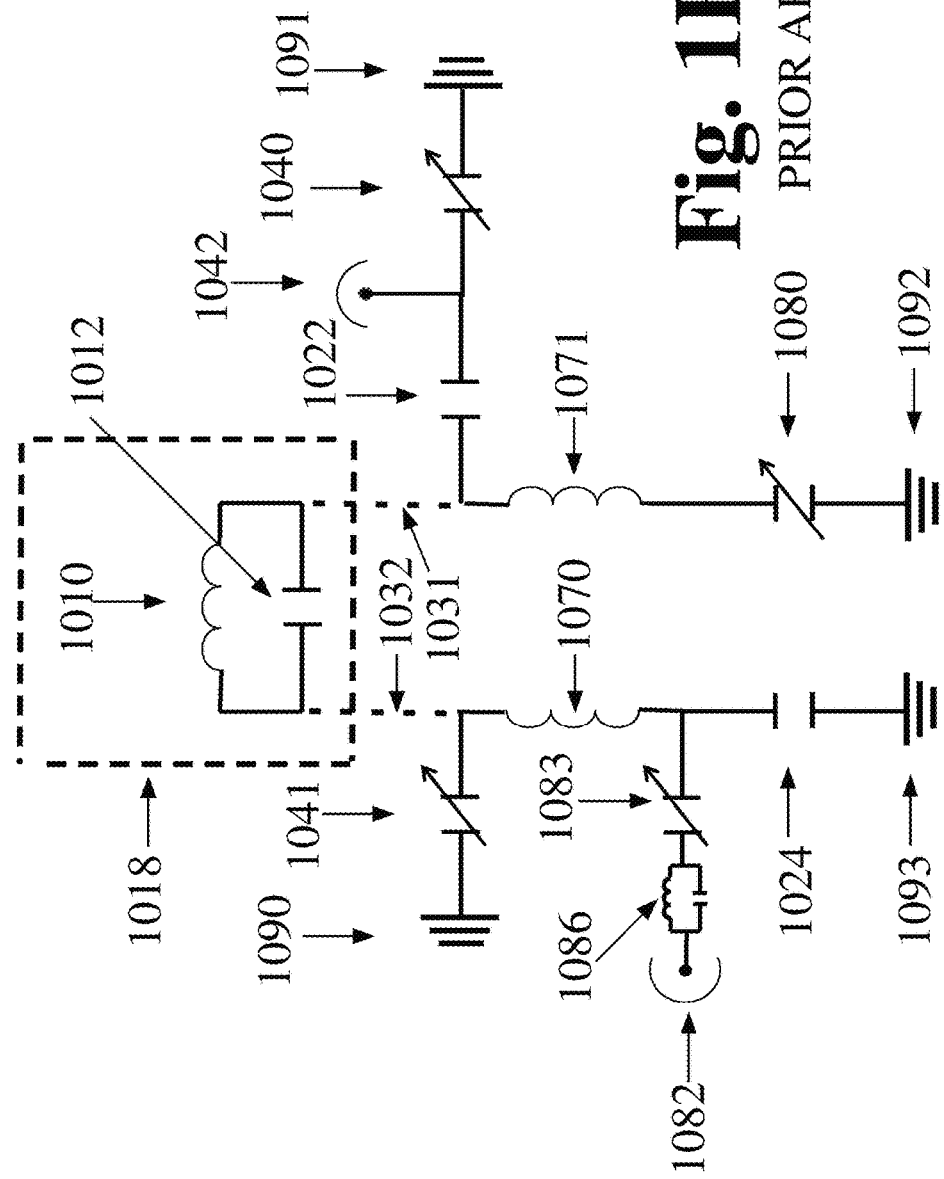
FIG. 1B is the schematic diagram of a double tuned circuit located in proximity to a sample resonator for a $^1H/^2H$ circuit.

FIG. 1B shows a double tuned circuit for a $^1$H/$^2$H resonance, with a sample inductor 1010, sample capacitor 1012, located in a sample resonator region, 1018. The resonator lead #1 1031, resonator lead #2 1032, connecting the sample inductor 1010 to inductor #1, 1070, and inductor #2, 1071, pass from the sample resonator region 1018, outside the sample resonator region, 1018. Outside the sample resonator region, 1018, are located a fixed tune capacitor, 1022, a tune variable capacitor, 1041, a match variable capacitor, 1040, a $^1$H fifty (50) Ohm port, 1042, an inductor #1, 1070, an inductor #2, 1071, a match variable capacitor, 1083, a tune variable capacitor, 1080, a high frequency block, 1086, a $^2$H fifty (50) Ohm port, 1082, a tune capacitor, 1024, ground (#1), 1090, ground (#2), 1091, ground (#3), 1092 and ground (#4) 1093. In the NMR experiment, the $B_0$ field needs to be very homogeneous, especially in the region of the NMR sample. In general for high resolution NMR this requires a homogeneity of approximately 1 part per billion. All of the materials that are in close proximity to the sample should have low susceptibility. For this reason the coil materials and built in capacitor are constructed from 'zero susceptibility' materials. Commercially available capacitors typically don't meet the 'zero susceptibility' requirement and as a result are kept below the lower insulator of the probe so as not to perturb the $B_0$ field. Accordingly, reducing the number of objects in the sample region is beneficial in implementing the NMR experiment. In this circuit because the variable capacitors are below the lower insulator these leads create flux which doesn't pass through the sample and hence represents a loss mechanism (or circuit fill factor loss) that depletes the S/N ratio. Typically removing this condition by placing all of the capacitance used to tune the coil in close proximity to the sample resonator improves the S/N ratio by approximately 10%, where approximate means ±two (2) percent.

It should be noted that the matching of the signal to fifty (50) Ohms with the circuitry shown in FIG. 1A and FIG. 1B is also an issue because the match capacitors are often bulky and are not typically susceptibility corrected. The tune capacitors (1022, 1041) shown in FIG. 1A and FIG. 1B are generally not constructed from zero susceptibility materials.

Figure 2A:
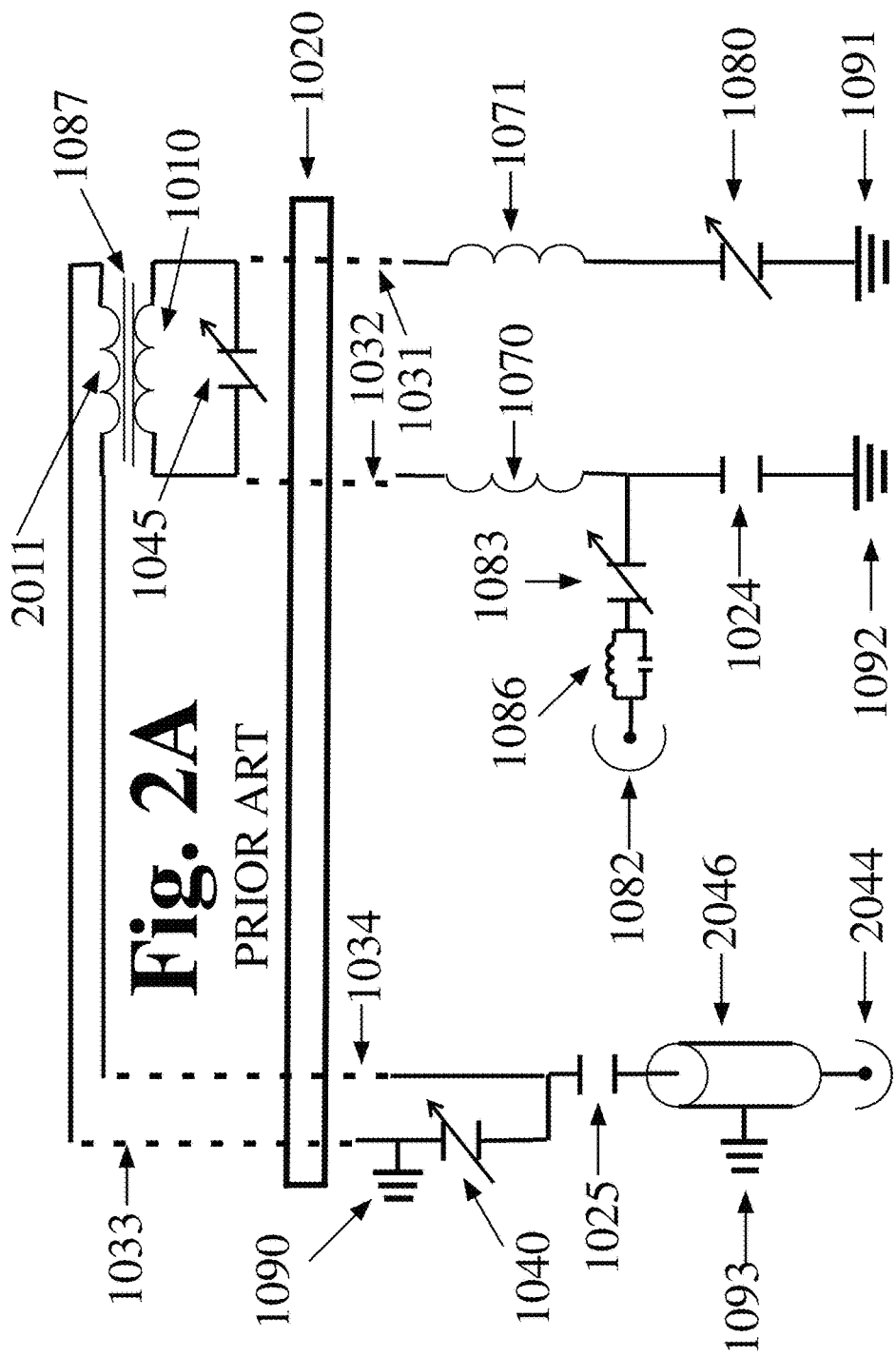
FIG. 2A is a schematic diagram of a double resonance circuit with a lower insulator for a $^1H/^{2H}$ circuit with inductive coupling to the sample coil.
Figure 2B:
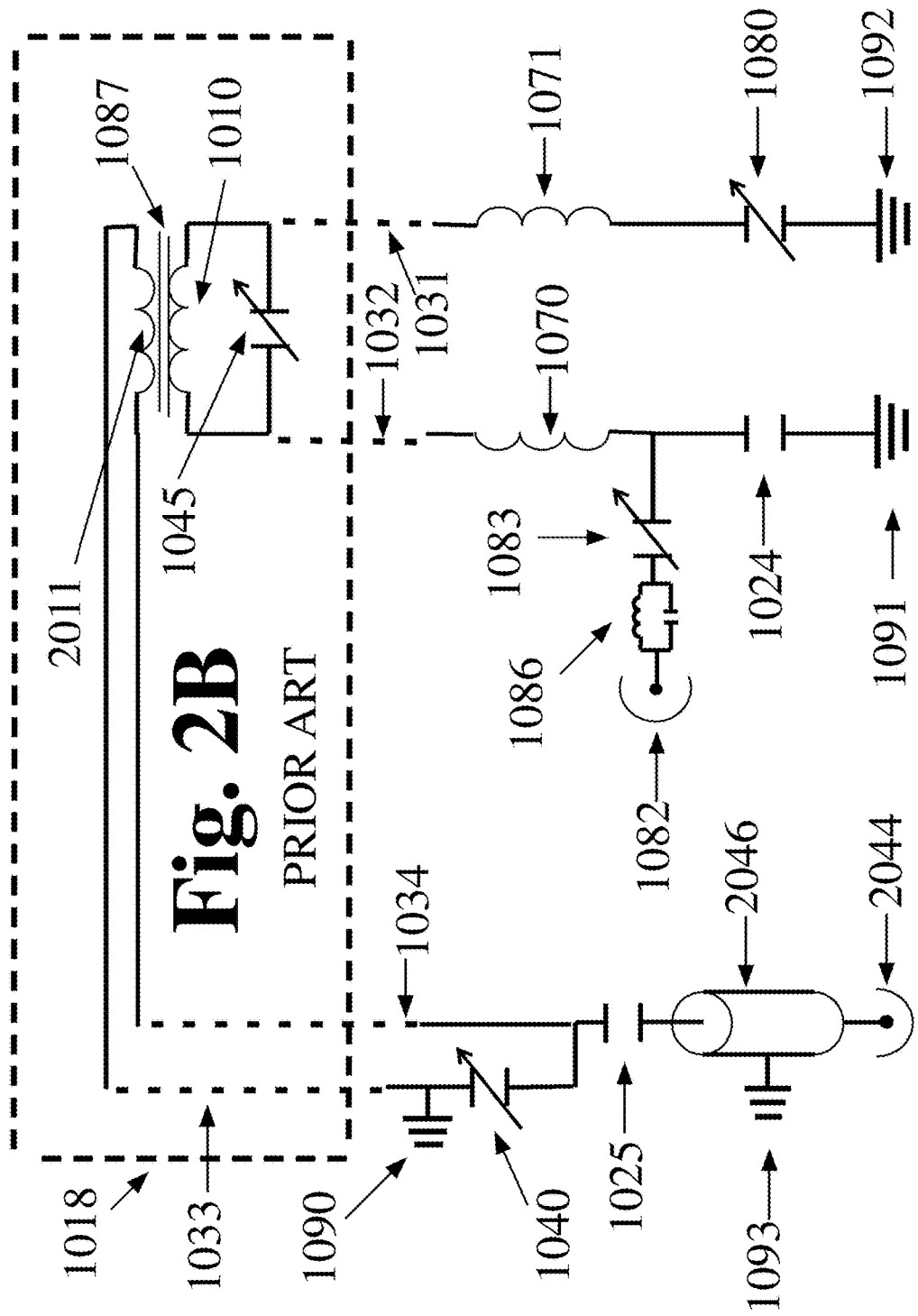
FIG. 2B is a schematic diagram of a double resonance circuit located in proximity to the sample resonator and inductive coupling loop for a $^1H/^2H$ with inductive coupling to the sample coil.

It should be noted that the matching of the signal to fifty (50) Ohms with the match circuitry shown in FIG. 2A and FIG. 2B is also an issue because the match capacitors are often bulky and are not typically susceptibility corrected. The tune capacitors, 1045 shown in FIG. 2A and FIG. 2B are generally constructed from zero susceptibility materials. These capacitors are typically built 'in-house' and in general have a limited tuning range and therefore don't have general applicability. In various embodiments of the invention, only the tune capacitor 1045 shown in FIG. 3A, FIG. 3B, FIG.

4A, FIG. 4B, FIG. 5A, FIG. 5B, FIG. 7A, FIG. 7B, FIG. 8A, FIG. 8B, FIG. 9A and FIG. 9B needs to be constructed from zero susceptibility materials.

FIG. 2A shows the magnetic pickup loop positioned above the lower insulator 1020, where the coupling loop 2011 is impinging on the sample space of the probe, according to an embodiment of the invention. It should also be recognized that if the order of the coils in this space is such that it is desired to couple to the inner coil in the presence of the outer coil, then arranging the three coils in a manner that minimizes interference can be extremely difficult. Having two pickup loops in the NMR probe, one for each coil is even more problematic.

FIG. 2A shows a schematic diagram of a double resonance circuit with a lower insulator 1020 for a $^1H/^2H$ with inductive coupling 1087 to a sample inductor 1010. The sample inductor 1010, the coupling loop 2011 and a tune variable capacitor 1045, are positioned above the lower insulator 1020. Resonator lead #1 1031, and resonator lead #2 1032 pass through the lower insulator, 1020 and connect the sample inductor, 1010 to inductor #1, 1070, and inductor #2, 1071. The left coupling loop lead, 1033 and the right coupling loop lead, 1034 also pass through the lower insulator, 1020 and connect the sample inductor, 1010 to the coupling capacitor, 1025, and a fifty (50) Ohm coax, 2046 and a $^1H$ fifty (50) Ohm port 2044. In various embodiments of the invention, the length of the left coupling loop lead, 1033 and the right coupling loop lead, 1034 are not necessarily the same. Below the lower insulator, 1020 are located inductor #1, 1070, inductor #2, 1071, a match variable capacitor, 1083, a tune variable capacitor, 1080, a high frequency block, 1086, a $^2H$ fifty (50) Ohm port, 1082, a tune capacitor, 1024, ground (#1), 1090, ground (#2), 1091, ground (#3), 1092 and ground (#4) 1093.

FIG. 2B shows a schematic diagram of a double tuned circuit with inductive coupling of 1087 for a $^1H/^2H$ resonance, with a sample resonator comprising a sample inductor 1010, and a tune variable capacitor 1045, and a coupling loop 2011 also located in the sample resonator region, 1018. Resonator lead #1 1031, and resonator lead #2 1032 pass from the sample inductor 1010, and the tune variable capacitor 1045, in the sample resonator region, 1018 and connect to inductor #1, 1070, inductor #2, 1071, positioned outside the sample resonator region, 1018. The left coupling loop lead, 1033 and the right coupling loop lead, 1034 also pass outside the sample resonator region, 1018 and connect the sample inductor, 1010 to the coupling capacitor, 1025, a fifty (50) Ohm coax, 2046 and a $^1H$ fifty (50) Ohm port 2044. Also outside the sample resonator region, 1018, are located a match variable capacitor, 1083, a tune variable capacitor, 1080, a high frequency block, 1086, a $^2H$ fifty (50) Ohm port, 1082.

In an embodiment of the present invention, for multiple tuned circuits the modes are present in all the inductors of the circuit so it is possible to couple to these inductors instead of the sample inductors. In an embodiment of the present invention, for multiple tuned circuits matching the circuit to any of the modes can be accomplished through any of the inductors in the circuit. As a result, for NMR circuits having coupling loops that are not in the sample space it is beneficial because these coils do not have to be (i) made of zero susceptibility material or (ii) as space intensive.

Figure 3A:
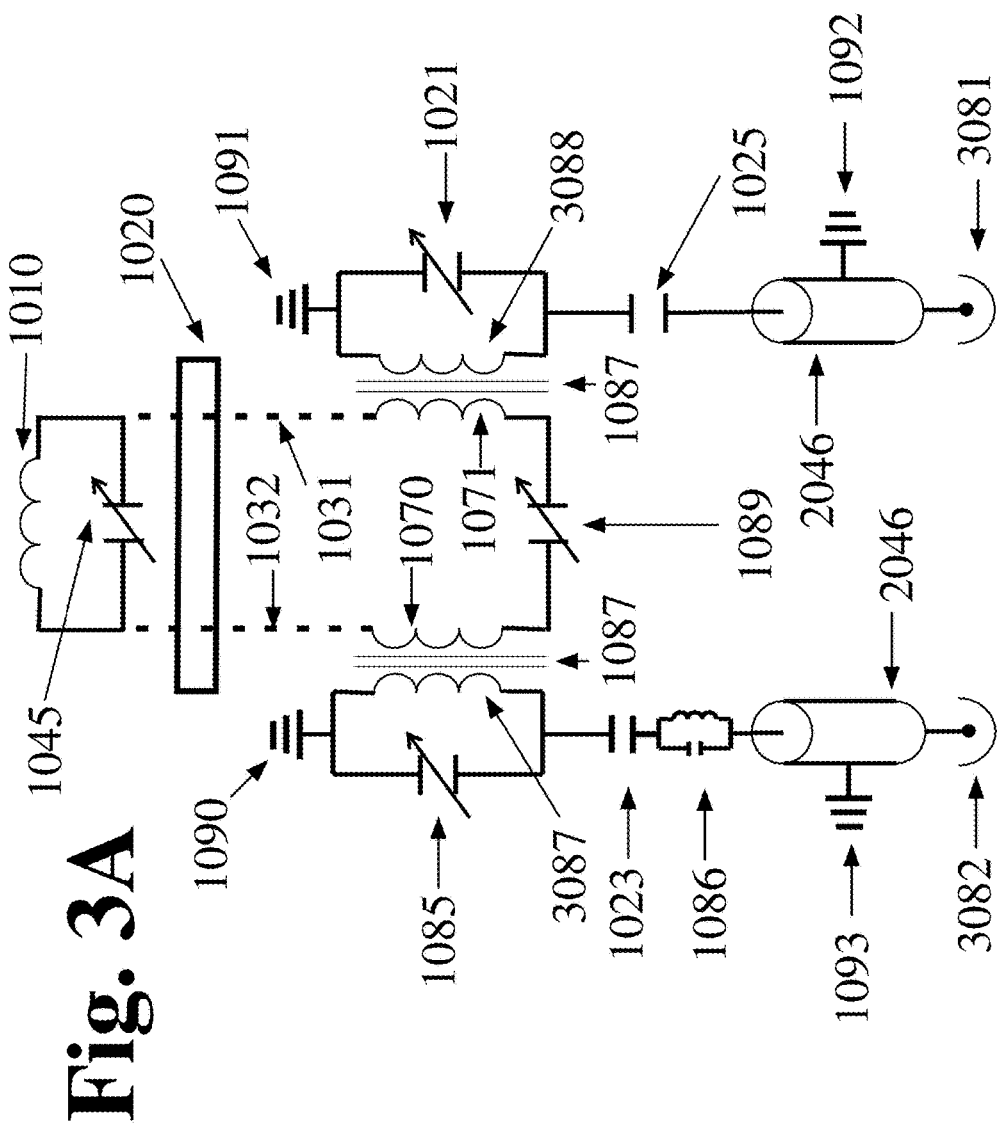
FIG. 3A is a schematic diagram showing a $^1H/^2H$ double tuned circuit with a sample coil located above a lower insulator with $^1H/^2H$ inductive coupling circuits located below the lower insulator, according to an embodiment of the present invention.
Figure 3B:
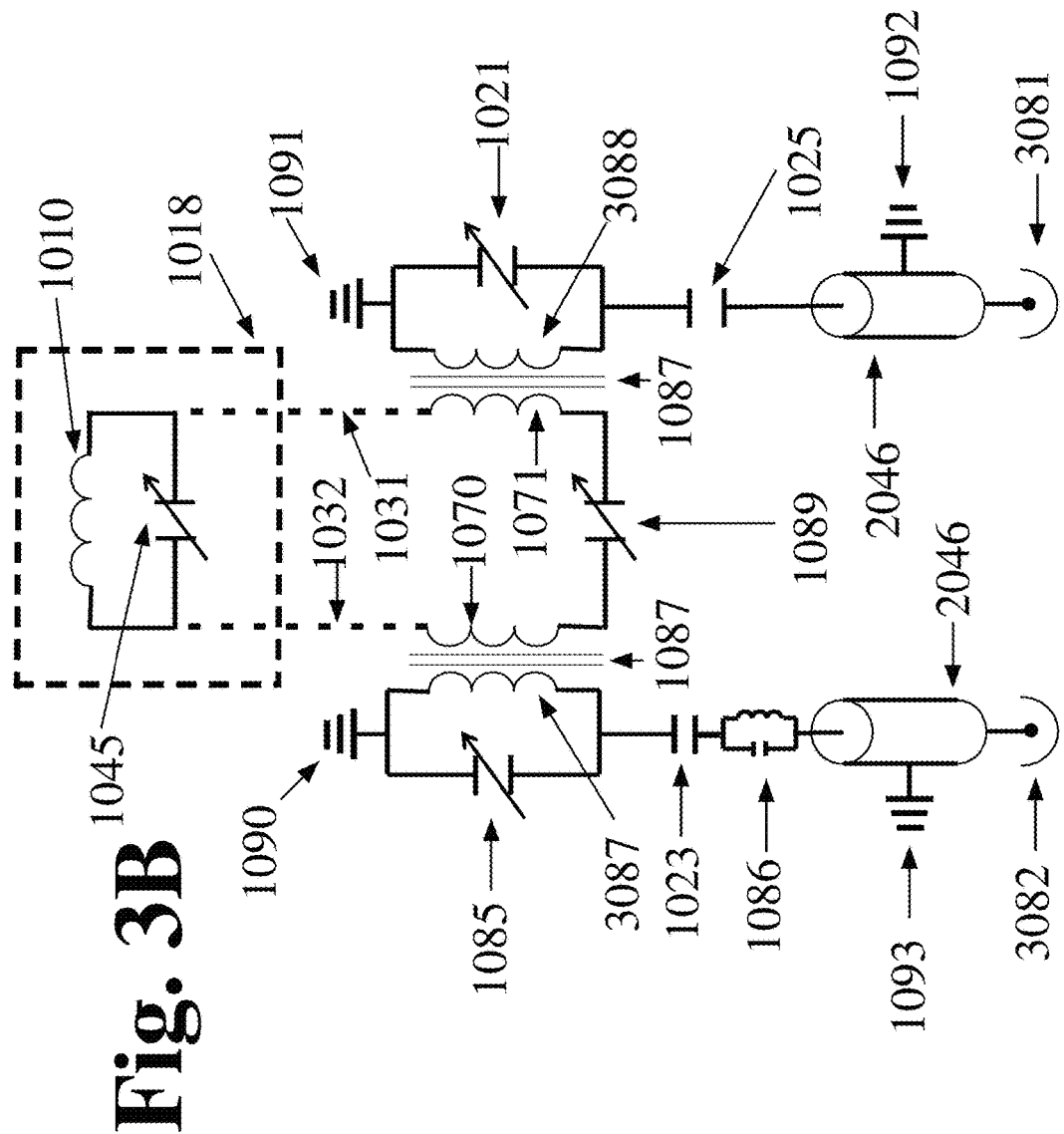
FIG. 3B is a schematic diagram showing a $^1H/^2H$ double tuned circuit with a sample coil located around the sample with $^1H/^2H$ inductive coupling circuits located outside the sample resonator, according to an embodiment of the present invention.

The inductive coupling of the circuits in FIG. 2A and FIG. 2B will perturb the RF homogeneity of the sample inductor, 1010. In an embodiment of the invention, in the circuits exemplified by the schematics shown in FIG. 3A and FIG. 3B this is not a problem, since the coupling is through secondary inductors, 1070 and 1071 according to various embodiments of the invention. Another benefit is that with all magnetic coupling the mutual inductance between the two coils perturbs the shape of the flux emanating from the coils. Clearly, any perturbation of the sample coil is undesirable. Accordingly, in various embodiments of the present invention, inductive coupling to the secondary coils is beneficial in that it does not (iii) impact the magnetic flux pattern of the sample coil. FIG. 3A and FIG. 3B show all the coupling to the double tuned circuit through the secondary coils according to an embodiment of the invention. Using this circuit arrangement allows for coupling below the lower threshold and/or outside the sample resonator region in a two coil probe with no space issues in the sample area.

FIG. 3A shows a schematic diagram of a double resonance circuit with a lower insulator 1020 for a $^1H/^2H$ circuit with inductive coupling to a sample inductor 1010 according to an embodiment of the invention. The sample inductor 1010 and a tune variable capacitor, 1045 are positioned above the lower insulator 1020. Resonator lead #1 1031, and resonator lead #2 1032 pass through the lower insulator, 1020 and connect the sample inductor, 1010 to inductor #1, 1070, and inductor #2, 1071. Below the lower insulator, 1020, inductor #1, 1070, inductively couples via 1087 to the coupling loop 3087. Here the match variable capacitor, 1085, is used to match the circuit to 50 Ohms via the coupling capacitor 1023, the 50 Ohm coax, 2046, and the 50 $^2H$ Ohm port, 3082. Inductor #2, 1071, couples via, 1087, to the coupling loop, 3088, where a match variable capacitor, 1021, is used to match the circuit to 50 Ohms via the coupling capacitor, 1025, fifty (50) Ohm coax, 1092, to the $^1H$ (50) Ohm port, 3081. Capacitor, 1089, is used to tune the $^2H$ resonance. Ground (#1), 1090, ground (#2), 1091, ground (#3), 1092, and ground (#4), 1093, are located in FIG. 3A. The ground points, 1090, 1091, 1092, 1093 associated with coupling loops, 3087, 3088 are not considered part of the resonant circuit since they do not contain high circulating current which is associated with resonant circuits. The circuit itself with the high circulating current has no ground points.

FIG. 3B shows a schematic diagram of a double resonance circuit with a sample region, 1018, for a $^1H/^2H$ circuit with inductive coupling to a sample inductor 1010 according to an embodiment of the invention. The sample inductor 1010 and a tune variable capacitor, 1045 are positioned in the sample region, 1018. Resonator lead #1 1031, and resonator lead #2 1032 pass through the sample region, 1018 and connect the sample inductor, 1010 to inductor #1, 1070, and inductor #2, 1071. Distal to, 1018. Inductor #1, 1070, inductively couples via 1087 to the coupling loop 3087. Here the match variable capacitor 1085 is used to match the circuit to 50 Ohms via the coupling capacitor 1023, the 50 Ohm coax, 2046, and the 50 $^2H$ Ohm port, 3082. Inductor #2, 1071, couples via, 1087, to the coupling loop, 3088, where a match variable capacitor, 1021, is used to match the circuit to 50 Ohms via the coupling capacitor, 1025, fifty (50) Ohm coax, 2046, to the $^1H$ (50) Ohm port, 3081. Capacitor, 1089, is used to tune the $^2H$ resonance. Ground (#1), 1090, ground (#2), 1091, ground (#3), 1092, and ground (#4), 1093, are located in FIG. 3A. The ground points, 1090, 1091, 1092, 1093 associated with coupling loops, 3087, 3088 are not considered part of the resonant circuit since they do not contain high circulating current which is associated with resonant circuits. The circuit itself with the high circulating current has no ground points.

Figure 3C:
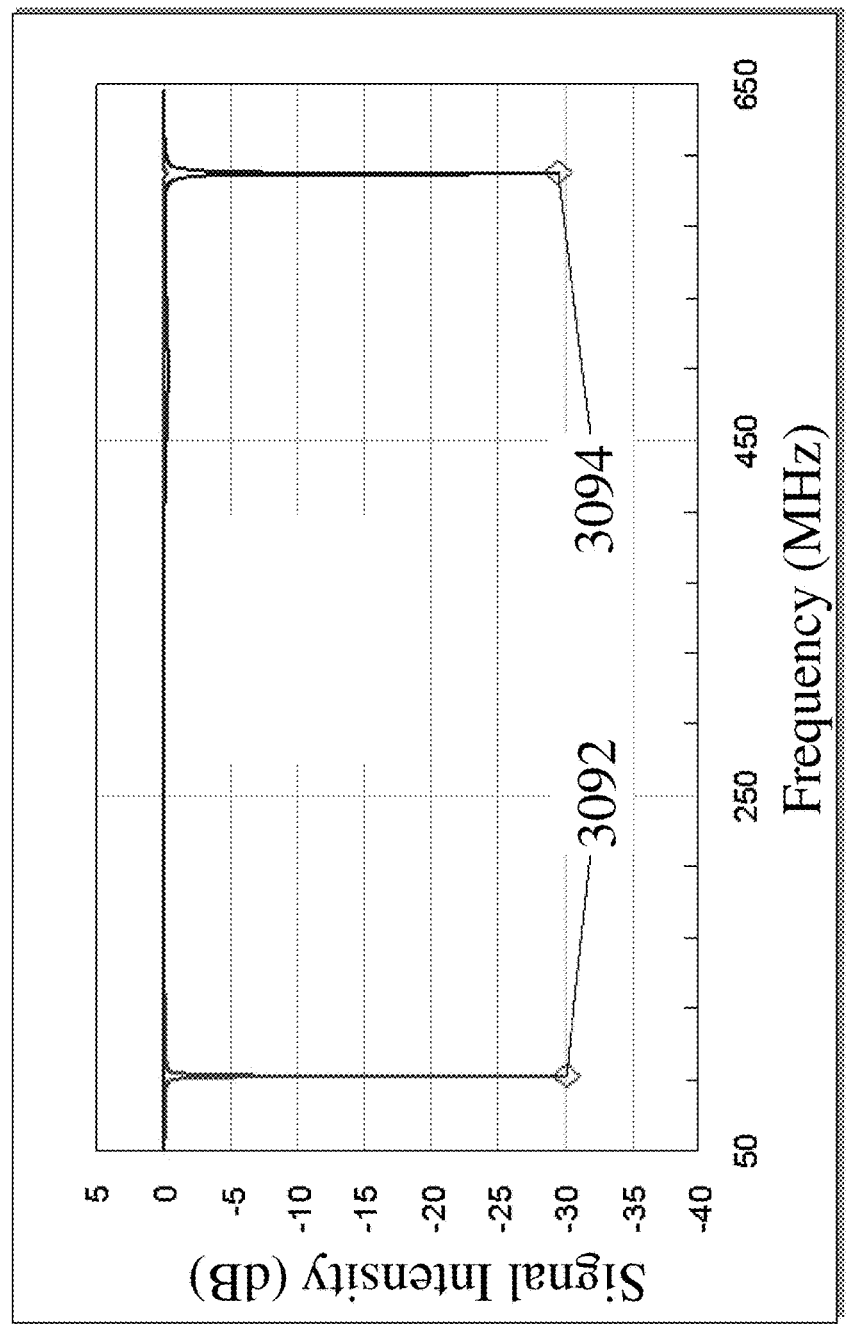
FIG. 3C is a two port plot overlay simulation showing the signal intensity versus the frequency for $^1H$ S(1,1) 3094 and $^2H$ S(2,2) 3092 based on the circuit shown in FIG. 3A and FIG. 3B, according to an embodiment of the present invention.

FIG. 3C shows a linear circuit simulation which was carried out based on the double tuned circuit shown in FIG.

3A and FIG. 3B. The plot in FIG. 3C is an overlay of the S(1,1) and S(2,2) plots, where the S(1,1) plot is labelled 3094, and the S(2,2) plot is 3092. FIG. 3C signal intensity versus the frequency shows two well defined minimums 3092, 3094 for $^1$H at 600 MHz and −29.39 dB 3094, and for $^2$H at 92.2 MHz and −30.03 dB 3092 respectively.

Figure 4A:
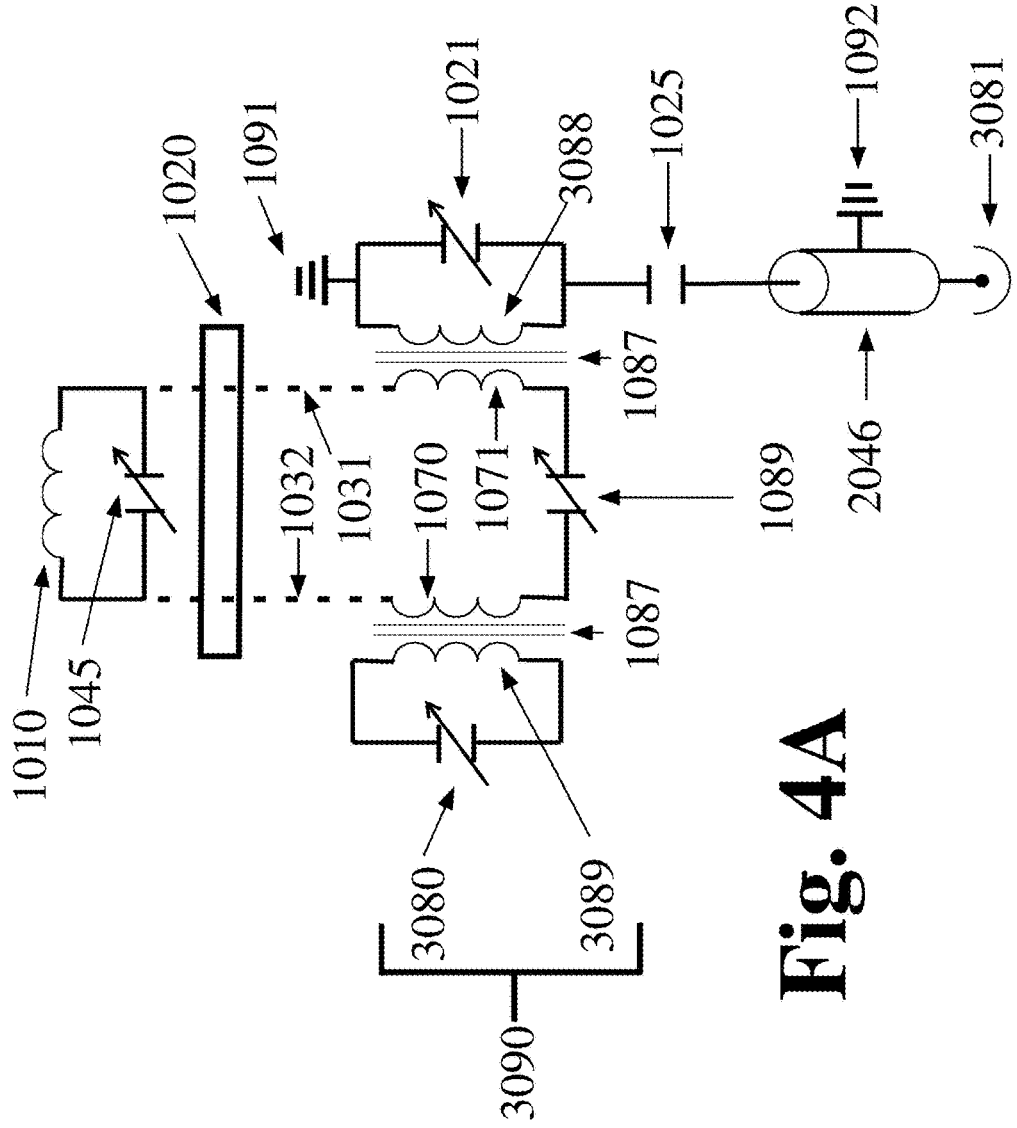
FIG. 4A is a schematic diagram showing a sample coil located above a lower insulator for a split resonance $^1H/^{19}F$ circuit with the inductive coupling circuit(s) located below the lower insulator, according to an embodiment of the present invention.
Figure 4B:
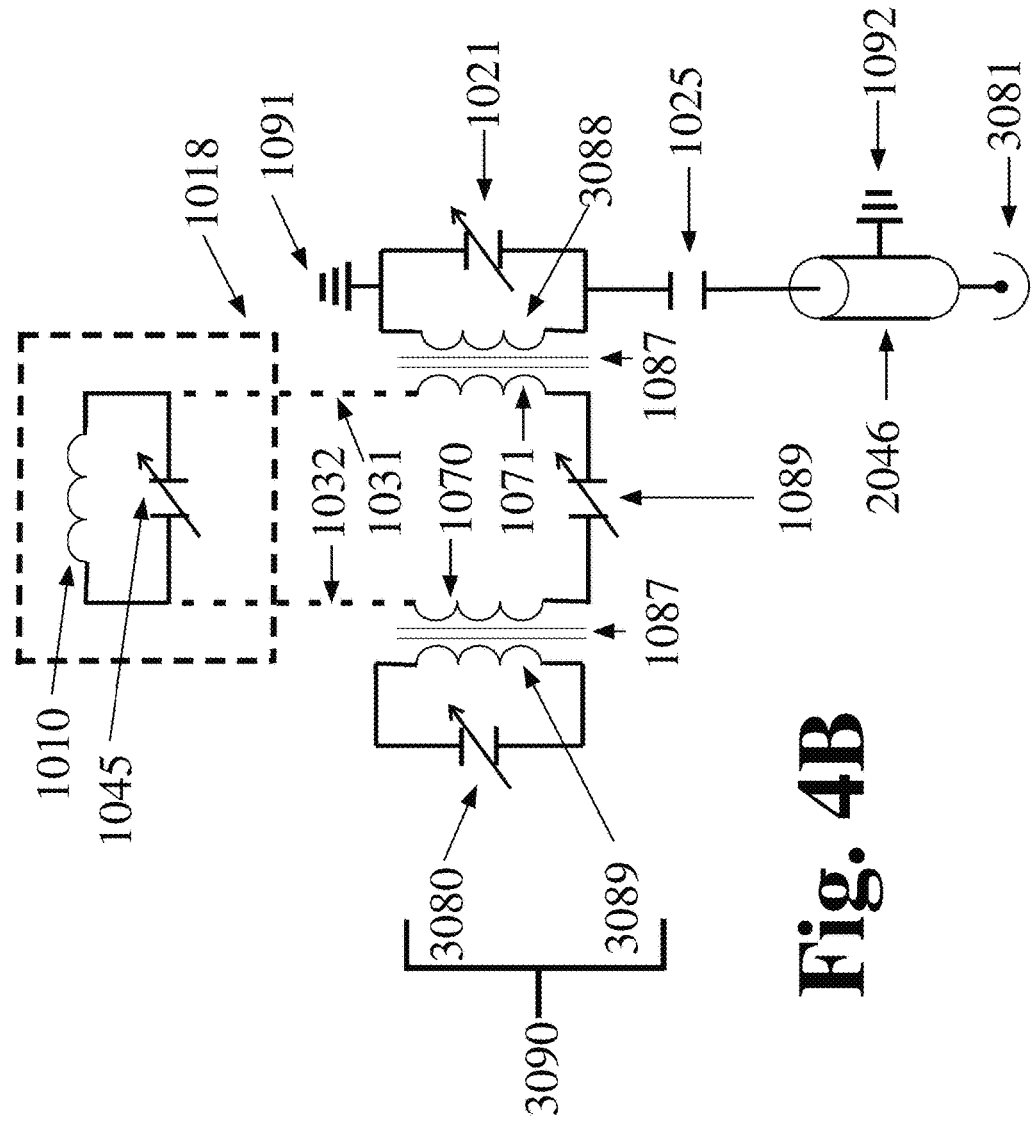
FIG. 4B is similar to FIG. 4A, a schematic diagram showing a sample coil located in the sample resonator region for a split resonance $^1H/^{19}F$ circuit with the inductive coupling circuit(s) located outside the sample resonator region, according to an embodiment of the present invention.

FIG. 4A and FIG. 4B show a coupling loop, where inductive coupling, 1087, can be used to match the circuit to a fifty (50) Ohm resistor for the high frequency fifty (50) Ohm port, the resonator, 3090, comprising the inductor, 3089, and the variable capacitor, 3080, can be used to split this resonance into two modes $^1$H and $^{19}$F using a shunt to adjust the coupling constant k according to an embodiment of the invention. Importantly, this circuit arrangement does not require that resonator, 3090, be constructed of zero susceptibility materials, the equivalent space considerations and the sample coil magnetic flux pattern is not perturbed. Further, the RF homogeneity of this coil is preserved even though the inductive coupling to the secondary coil produces another mode in the circuit.

Figure 4C:
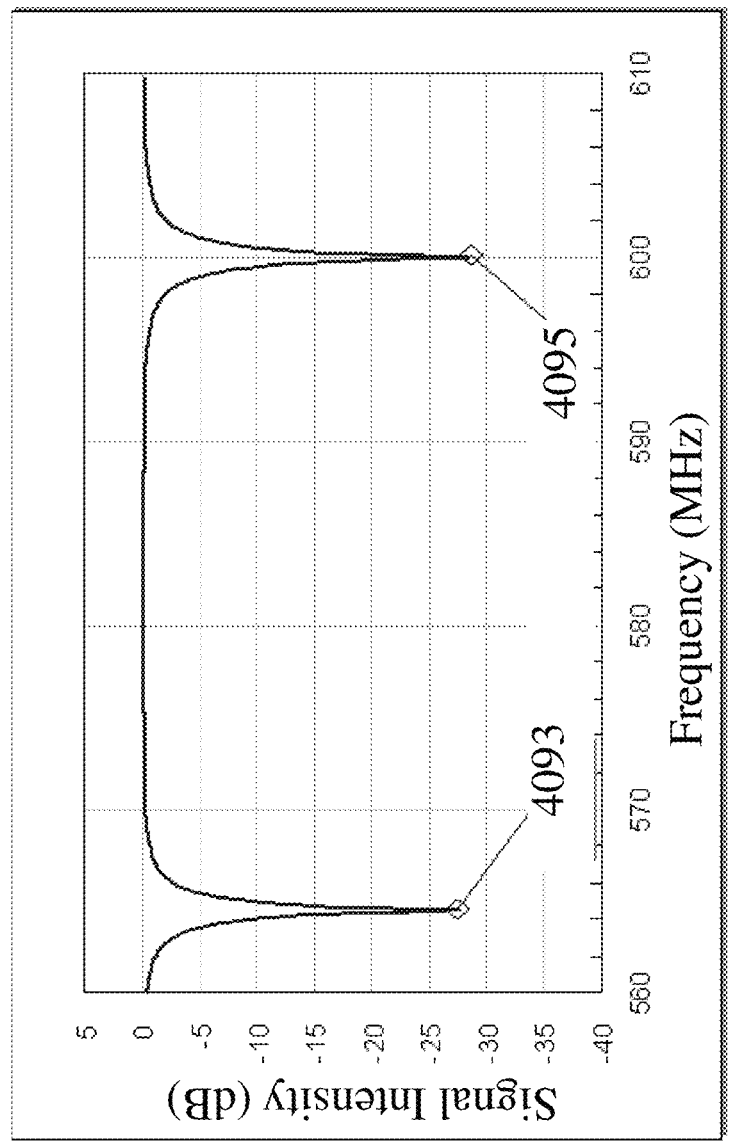
FIG. 4C is a single port plot S(1,1) simulation showing the signal intensity versus the frequency for two resonances $^1H$ 4095 and $^{19}F$ 4093 based on the circuit shown in FIG. 4A and FIG. 4B, according to an embodiment of the present invention.

FIG. 4A shows a schematic diagram of a split resonance inductive coupling circuit with a lower insulator, 1020 for $^1$H/$^{19}$F with inductive coupling. The sample inductor, 1010 and a tune variable capacitor, 1045 are positioned above the lower insulator, 1020. Resonator lead #1 1031, and resonator lead #2, 1032 pass through the lower insulator, 1020 and connect the sample inductor, 1010, to inductor #1, 1070, and inductor #2, 1071. Below the lower insulator, 1020, inductor #1, 1070, and inductor #2, 1071, inductively couple, 1087 through the $^1$H coupling loop, 3088, where a $^1$H match variable capacitor 1021, a coupling capacitor 1025, a fifty (50) Ohm coax, 2046, are used to match the high frequency circuit to 50 ohms, through the $^1$H 50 ohm port, 3081. The resonator 3090, comprised of inductor, 3089, and capacitor, 3080, splits the primary resonance into two modes via coupling from 1087 to inductor 1070, $^1$H and $^{19}$F. The variable capacitors 1045 and 1089 are used to tune the $^1$H resonance. FIG. 4C is an S(1,1) plot which shows a linear circuit simulation which is carried out based on the simultaneous double tune circuit shown in FIG. 4A according to an embodiment of the invention. The plot of signal intensity versus the frequency shows two peaks 4093, 4095 with minimums for $^1$H at 600 MHz and −28.55 dB 4095, and for $^{19}$F at 564.5 MHz and −27.36 dB 4093. In FIG. 4A, the ground points, 1091, 1092 associated with coupling loops, 3088 are not considered part of the resonant circuit since they do not contain a high circulating current which is associated with resonant circuits.

FIG. 4B shows a schematic diagram of a split resonance circuit without a lower insulator for $^1$H/$^{19}$F with inductive coupling. The sample inductor, 1010 and a tune variable capacitor, 1045, are positioned in the sample region, 1018. Resonator lead #1 1031, and resonator lead #2, 1032 pass from the region, 1018 and connect the sample inductor, 1010 to inductor #1, 1070, and inductor #2, 1071. Outside the region, 1018, inductor #2, 1071, inductively couple, 1087 through the coupling loop, 3088, where a match variable capacitor 1021, a coupling capacitor 1025, a fifty (50) Ohm coax, 2046, match the circuit to a $^1$H 50 Ohm port, 3081. A high frequency resonator 3090 comprising the inductor, 3089, and capacitor, 3080, are used to split the circuit primary mode into two modes $^1$H and $^{19}$F via coupling through 1087 to inductor #1, 1070. Variable capacitors 1045 and 1089 are use to tune the circuit to the $^1$H resonance. In FIG. 4B, the ground points, 1091, 1092 associated with the coupling loop, 3088, are not considered part of the resonant circuit since they do not contain a high circulating current which is associated with resonant circuits.

Figure 5A:
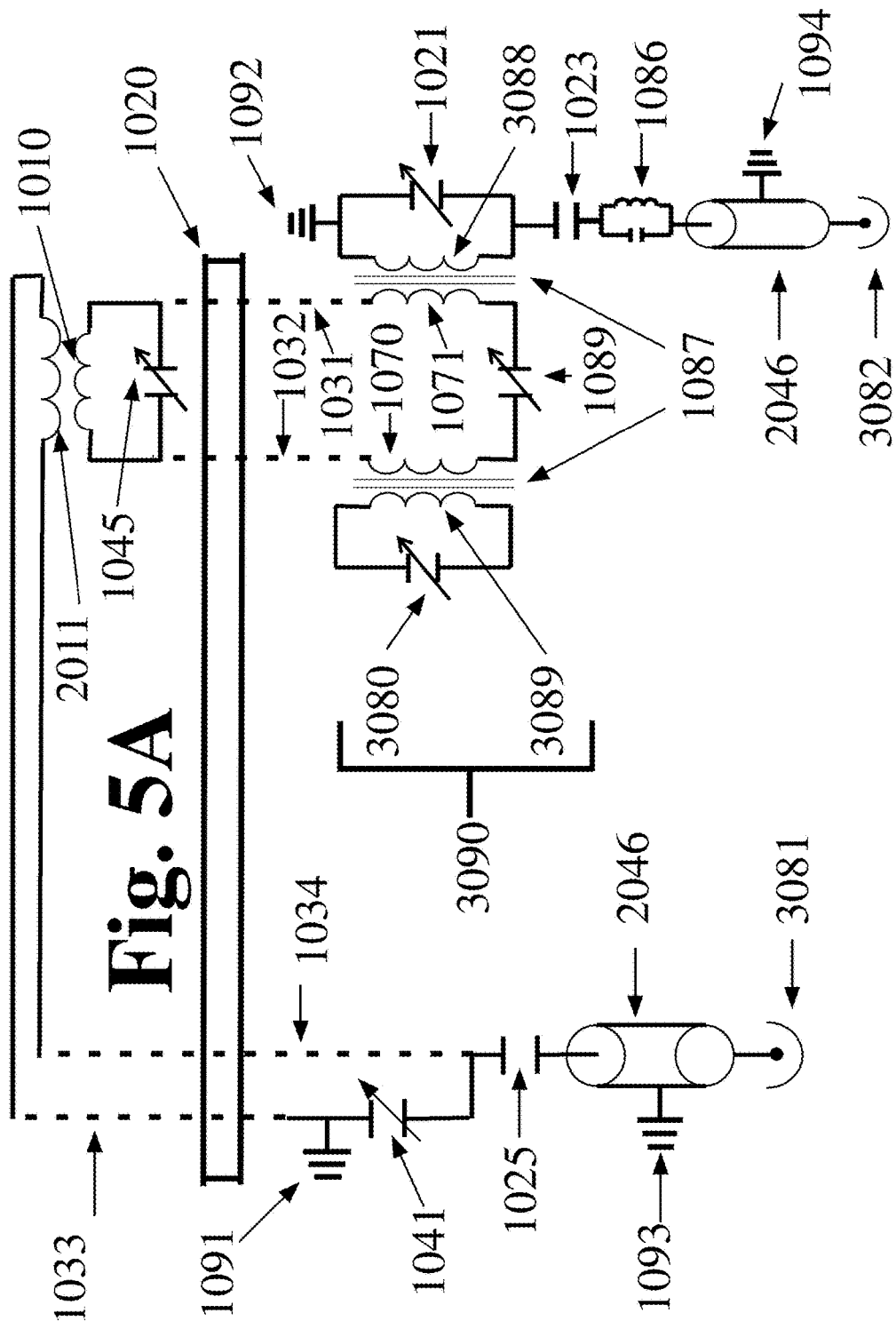
FIG. 5A is a schematic diagram showing a sample coil and a coupling loop located above a lower insulator for a split resonance circuit with the inductive coupling circuits located below the lower insulator, according to an embodiment of the present invention.

FIG. 5A is a schematic diagram for a split resonance circuit showing a sample coil, 1010 and a coupling loop, 2011 located above a lower insulator 1020, according to an embodiment of the invention. The sample inductor 1010, the coupling loop 2011 and a tune variable capacitor 1045, are positioned above the lower insulator 1020. Resonator lead #1 1031, and resonator lead #2 1032 pass through the lower insulator, 1020 and connect the sample inductor, 1010 to inductor #1, 1070, and inductor #2, 1071. The left coupling loop lead, 1033 and the right coupling loop lead, 1034 also pass through the lower insulator, 1020 and connect, 2011, to the coupling capacitor, 1025, the match variable, 1041, a fifty (50) Ohm coax, 2046, and a $^1$H fifty (50) Ohm port, 3081. The $^1$H circuit is matched with variable capacitor, 1041. In various embodiments of the invention, the length of the left coupling loop lead, 1033, and the right coupling loop lead, 1034, are not necessarily the same. Below the lower insulator, 1020 are located inductor #1, 1070, inductor #2, 1071, a match variable capacitor, 1021, a high frequency block, 1086, a 50 Ohm coax, 2046, a $^2$H fifty (50) Ohm port, 3082, a coupling capacitor, 1023. Ground (#1), 1091, ground (#2), 1092, ground (#3), 1093 and ground (#4) 1094. The coupling loop 2011 is inductively coupled via, 1087, to the sample coil, 1010, to form the $^1$H 50 Ohm port. In an embodiment of the invention, the resonator 3090 comprised of capacitor, 3080, and inductor, 3089, couples via, 1087, to inductor #1, 1070, to split the high frequency resonance mode into two distinct resonances, i.e., $^1$H and $^{19}$F using a shunt to adjust the coupling constant k. The splitting will depend on the proximity of the resonator, 3090, to the inductor and can be modified by moving the resonator, 3090, closer or further away, via a shunt, to achieve the desired splitting and coupling constant k. The variable capacitor, 1089, is used to tune the $^2$H resonance. In FIG. 5A, 1025 and, 1023, are coupling capacitors for the coupling loops, 2011, and, 3088, respectively. In FIG. 5A, the ground points, 1091, 1092, 1093, 1094 associated with coupling loop, 3088, and 2011 are not considered part of the resonant circuit since they do not contain a high circulating current which is associated with resonant circuits.

FIG. 5B is a schematic diagram for a split resonance circuit showing a sample coil, 1010 and a coupling loop, 2011 located in sample region 1019, according to an embodiment of the invention. The sample inductor 1010, the coupling loop 2011 and a tune variable capacitor 1045, are positioned in sample region, 1019. Resonator lead #1 1031, and resonator lead #2 1032 pass through region, 1019, and connect the sample inductor, 1010 to inductor #1, 1070, and inductor #2, 1071. The left coupling loop lead, 1033 and the right coupling loop lead, 1034 also pass through the region, 1019 and connect, 2011, to the coupling capacitor, 1025, the match variable, 1041, a fifty (50) Ohm coax, 2046, and a $^1$H fifty (50) Ohm port, 2044. The $^1$H circuit is matched with variable capacitor, 1041. In various embodiments of the invention, the length of the left coupling loop lead, 1033, and the right coupling loop lead, 1034, are not necessarily the same. Below the lower insulator, 1020 are located inductor #1, 1070, inductor #2, 1071, a match variable capacitor, 1021, a high frequency block, 1086, a 50 Ohm coax, 2046, a $^2$H fifty (50) Ohm port, 3082, a coupling capacitor, 1023. Ground (#1), 1090, ground (#2), 1092, ground (#3), 1093 and ground (#4) 1094. The coupling loop 2011 is inductively coupled via, 1087, to the sample coil, 1010, to form the $^1$H 50 Ohm port. In an embodiment of the invention, the resonator 3090 comprised of capacitor, 3080, and inductor, 3089, couples via, 1087, to inductor #1, 1070, to split the high frequency resonance mode into two distinct resonances, i.e., $^1$H and $^{19}$F using a shunt to adjust the coupling constant k. The splitting will depend on the proximity of the resonator, 3090, to the inductor and can be modified by moving the resonator, 3090, closer or further away, via a shunt, to achieve the desired splitting and coupling constant k. The variable capacitor, 1089, is used to tune the $^2$H resonance. In FIG. 5A, 1025 and, 1023, are coupling capacitors for the coupling loops, 2011, and, 3088, respectively. In FIG. 5B, the ground points, 1090, 1092, 1093, 1094 associated with coupling loop, 3088, and 2011 are not considered part of the resonant circuit since they do not contain a high circulating current which is associated with resonant circuits.

Figure 6A:
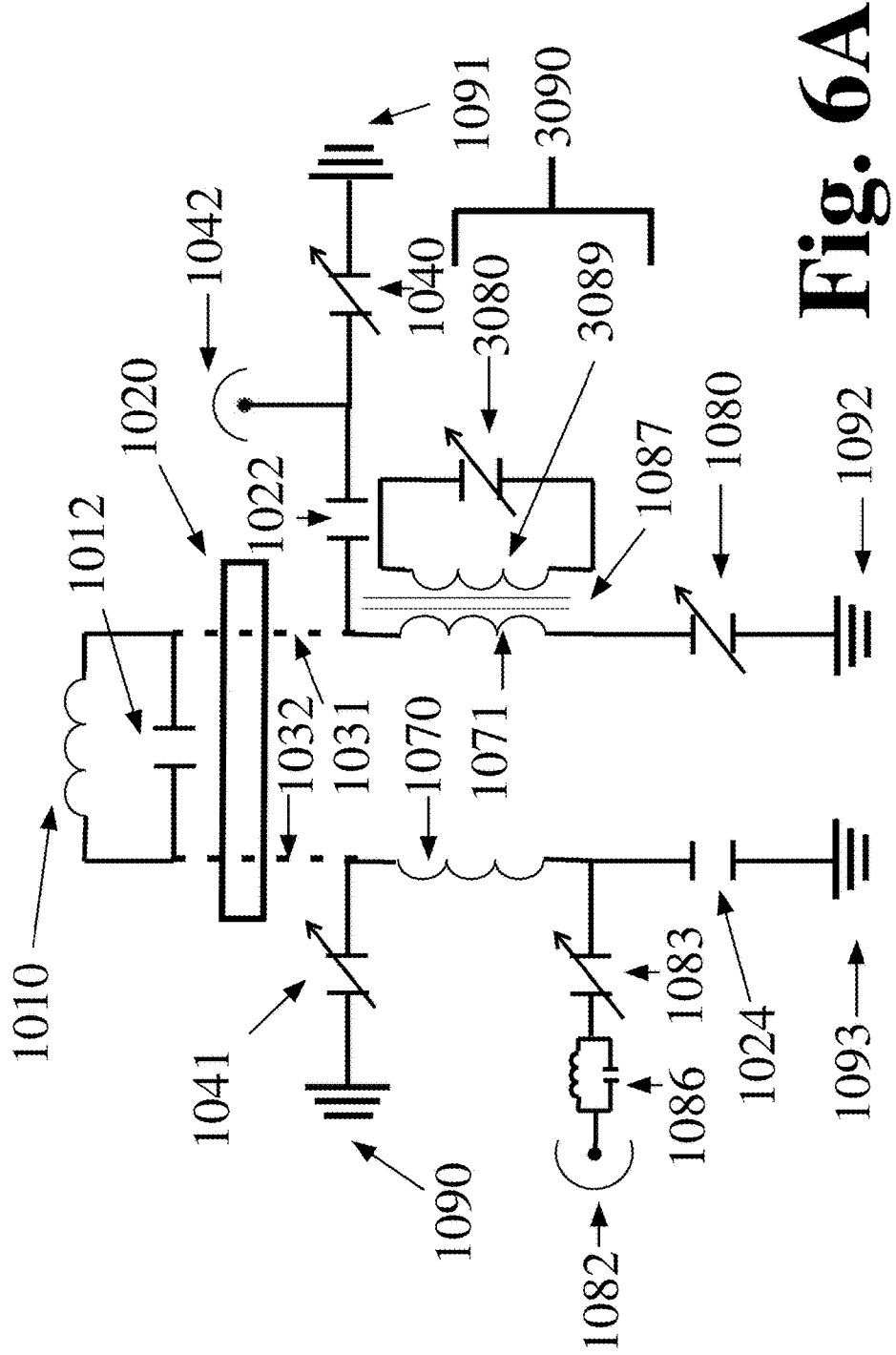
FIG. 6A is a schematic diagram showing a sample coil located above a lower insulator with the inductive coupling circuit(s) located below the lower insulator where the resonator splits the high frequency resonance into two modes, $^1H$ and $^{19}F$, according to an embodiment of the present invention.

FIG. 6A is a schematic diagram similar to FIG. 1A. A sample inductor, 1010, and sample capacitor, 1012, are positioned above the lower insulator, 1020. The resonator lead #1 1031, and resonator lead #2, 1032 pass through the lower insulator, 1020 and connect the sample inductor, 1010, to inductor #1, 1070, and inductor #2, 1071. In various embodiments of the invention, the length of the resonator lead #1, 1031, and resonator lead #2, 1032 are not necessarily the same. Below the lower insulator, 1020 are located a fixed tune capacitor, 1022, a tune variable capacitor, 1041, a match variable capacitor, 1040, a $^1$H fifty (50) Ohm port, 1042, a inductor #1, 1070, inductor #2, 1071, a match variable capacitor, 1083, a tune variable capacitor, 1080, a high frequency block, 1086, a $^2$H fifty (50) Ohm port, 1082, a tune capacitor, 1024, ground (#1), 1090, ground (#2), 1091, ground (#3), 1092 and ground (#4) 1093. Here in addition to the components in FIG. 1A a resonator, 3090, comprised of and inductor, 3089, and a capacitor, 3080, the resonator, 3090, is used to inductively couple, 1087 to inductor #2, 1071. This inductive coupling, 1087, can split the high frequency mode into two resonances, e.g., $^{19}$F and $^1$H using a shunt to adjust the coupling constant k, according to an embodiment of the invention. This coupling, 1087 can be modified by moving inductive coupling loop 3089 closer or further away from inductor #2, 1071, to achieve the desired splitting and coupling constant k. In FIG. 6A, the ground points, 1090, 1091, 1092, 1093 are associated with the circuit.

Figure 6B:
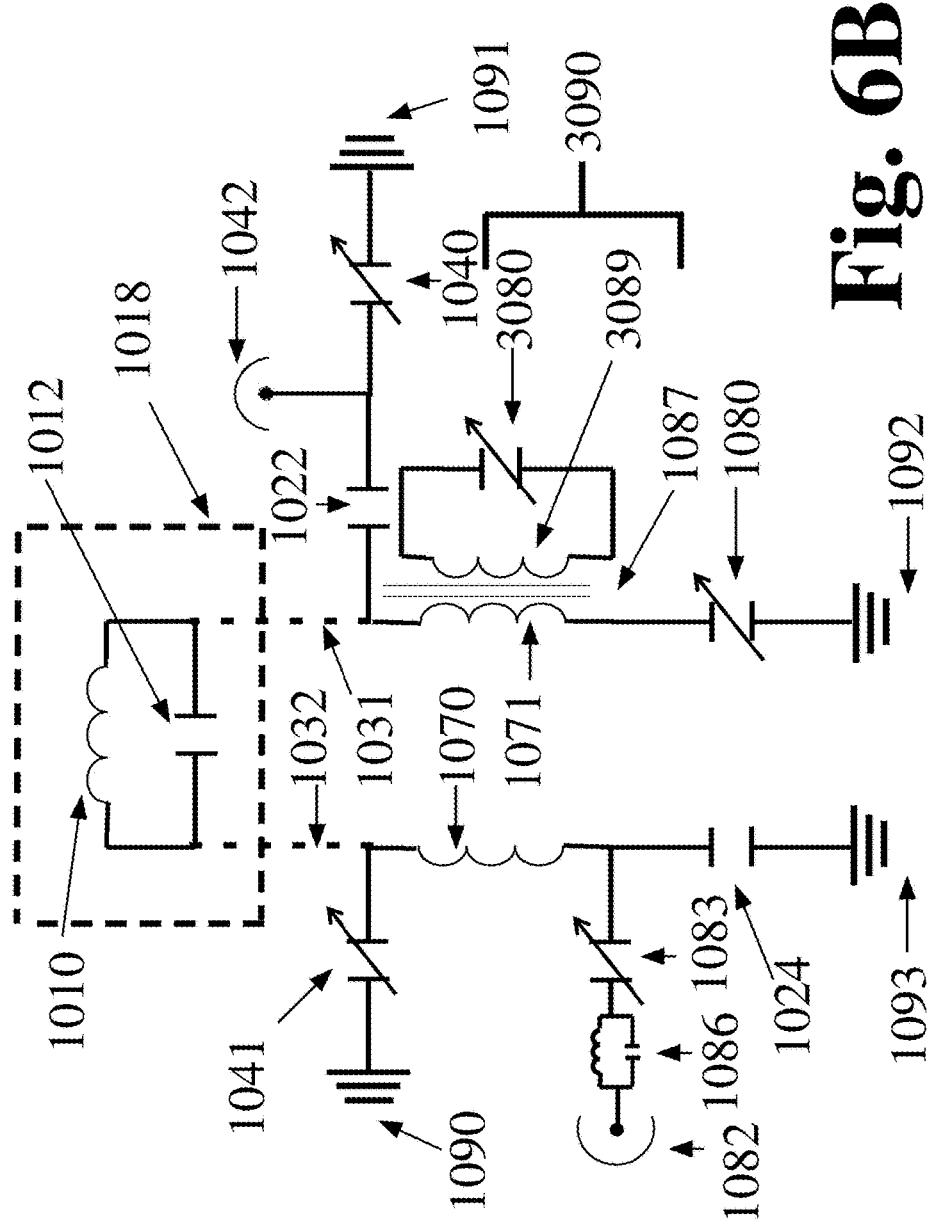
FIG. 6B is a schematic diagram showing a sample coil located in the sample resonator region with the inductive coupling circuit(s) located outside the sample resonator region in a manner similar to FIG. 6A, according to an embodiment of the present invention.

FIG. 6B is a schematic diagram that is similar to FIG. 1A, where a sample resonator region, 1018 is comprised of a sample inductor, 1010, and a sample capacitor, 1012. The resonator lead #1 1031, resonator lead #2 1032, connecting the sample inductor 1010 to inductor #1, 1070, and inductor #2, 1071, pass from the sample resonator region, 1018. In various embodiments of the invention, the length of the resonator lead #1, 1031, and resonator lead #2, 1032 are not necessarily the same. In FIG. 6B, outside the sample resonator region, 1018, a tune variable capacitor, 1041, a match variable capacitor, 1040, a $^1$H fifty (50) Ohm port, 1042, a inductor #1, 1070, a inductor #2, 1071, a match variable capacitor, 1083, a tune variable capacitor, 1080, a high frequency block, 1086, a $^2$H fifty (50) Ohm port, 1082, a tune capacitor, 1024, ground (#1), 1090, ground (#2), 1091, ground (#3), 1092 and ground (#4) 1093. In FIG. 6B, the ground points, 1090, 1091, 1092, 1093 are associated with the circuit. Here in addition to these elements is a resonator, 3090, distal to, 1018, is used to split the $^1$H resonance into two modes, $^1$H and $^{19}$F, coupling to, inductor #2, 1071, via 1087.

Figure 7A:
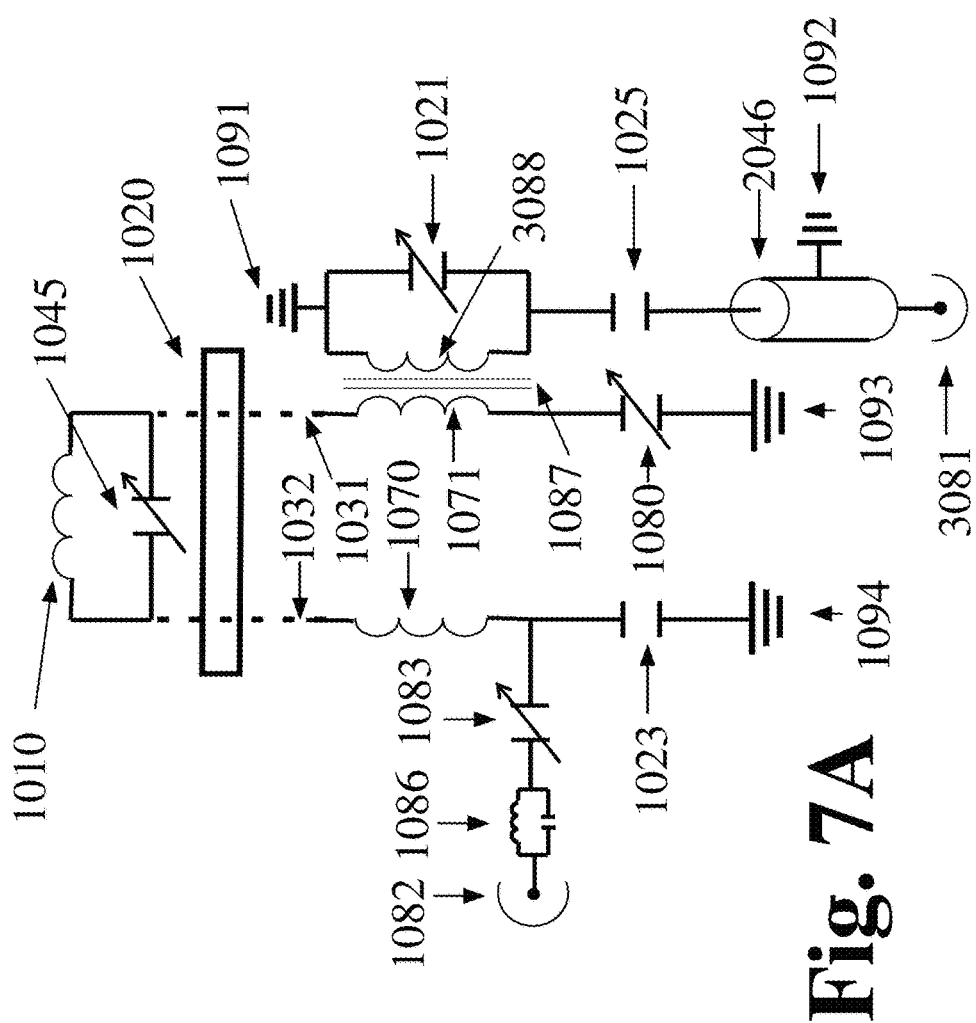
FIG. 7A is a schematic diagram showing a sample coil located above a lower insulator with the inductive coupling circuit(s) located below the lower insulator, where the $^1H$ port, emanates from the inductive coupling of inductor according to an embodiment of the present invention.

FIG. 7A is a schematic diagram showing a sample coil 1010 and sample capacitor 1045 located above a lower insulator, 1020. The sample inductor, 1010 and a tune variable capacitor, 1045 are positioned above the lower insulator, 1020. Resonator lead #1 1031, and resonator lead #2, 1032 pass through the lower insulator, 1020 and connect the sample inductor, 1010 to inductor #1, 1070, and inductor #2, 1071. Below the lower insulator, 1020, inductor #2, 1071, inductively couples, 1087 to the tuned circuit through the coupling loop, 3088, where a match variable capacitor 1021, a coupling capacitor 1025, a fifty (50) ohm coax, 2046, are used to complete the 50 Ohm $^1$H port, 3081. Below the lower insulator, 1020 are also located a match variable capacitor, 1083, a tune capacitor, 1023, a high frequency block, 1086, a $^2$H fifty (50) Ohm port, 1082, ground (#1), 1091, ground (#2), 1092, ground (#3), 1093 and ground (#4) 1094. In this circuit a coupling loop 3088 inductively couples to inductor #2, 1071. In FIG. 7A, the ground points, 1091, and 1092 associated with coupling loop, 3088 are not considered part of the resonant circuit since they do not contain a high circulating current which is associated with resonant circuits. Ground points 1093 and 1094 are considered part of the resonant circuit.

Figure 7B:
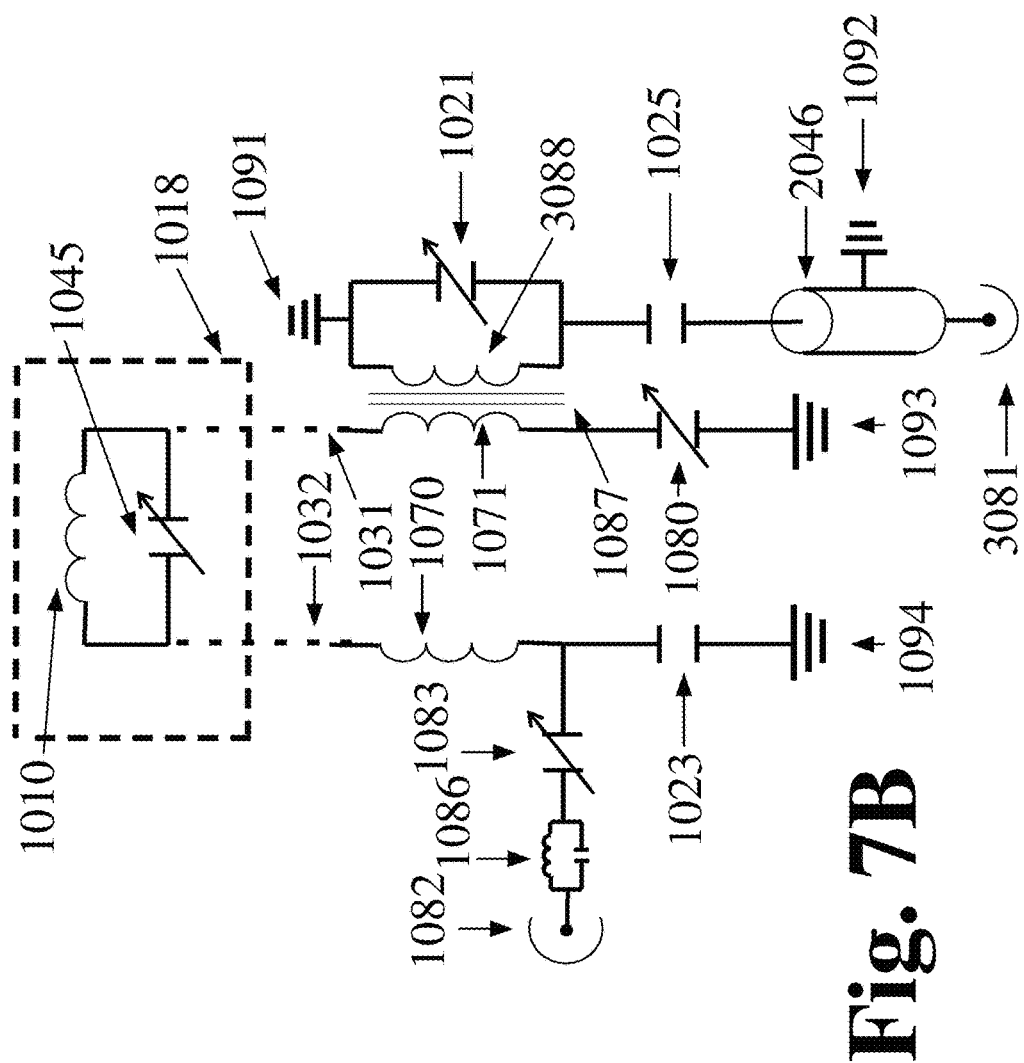
FIG. 7B is a schematic diagram showing a sample coil located in the sample resonator region with the inductive coupling circuit(s) located outside the sample resonator in a manner similar to FIG. 7A, according to an embodiment of the present invention.

FIG. 7B shows a schematic diagram that is similar to FIG. 7A, where a sample resonator region, 1018 is comprised of a sample inductor, 1010, and a sample capacitor, 1045. The resonator lead #1 1031, resonator lead #2 1032, connecting the sample inductor 1010 to inductor #1, 1070, and inductor #2, 1071, pass from the sample resonator region, 1018 outside the sample resonator region, 1018. In various embodiments of the invention, the length of the resonator lead #1, 1031, and resonator lead #2, 1032 are not necessarily the same. In FIG. 7B, outside the sample resonator region, 1018, are located, inductor #2, 1071, which inductively couples, 1087 to the tuned circuit through the coupling loop, 3088, where a match variable capacitor 1021, a coupling capacitor 1025, a fifty (50) Ohm coax, 2046 are used to tune the circuit. Outside the sample resonator region, 1018 are also located a match variable capacitor, 1083, a high frequency block, 1086, a tune capacitor, 1023, a $^2$H fifty (50) Ohm port, 1082, ground (#1), 1091, ground (#2), 1092, ground (#3), 1093, and ground (#4) 1094. In FIG. 7B, the ground points, 1091, 1092, associated with coupling loop, 3088 are not considered part of the resonant circuit since they do not contain a high circulating current which is associated with resonant circuits. Ground points, 1093, and 1094 are considered part of the resonant circuit.

Figure 8A:
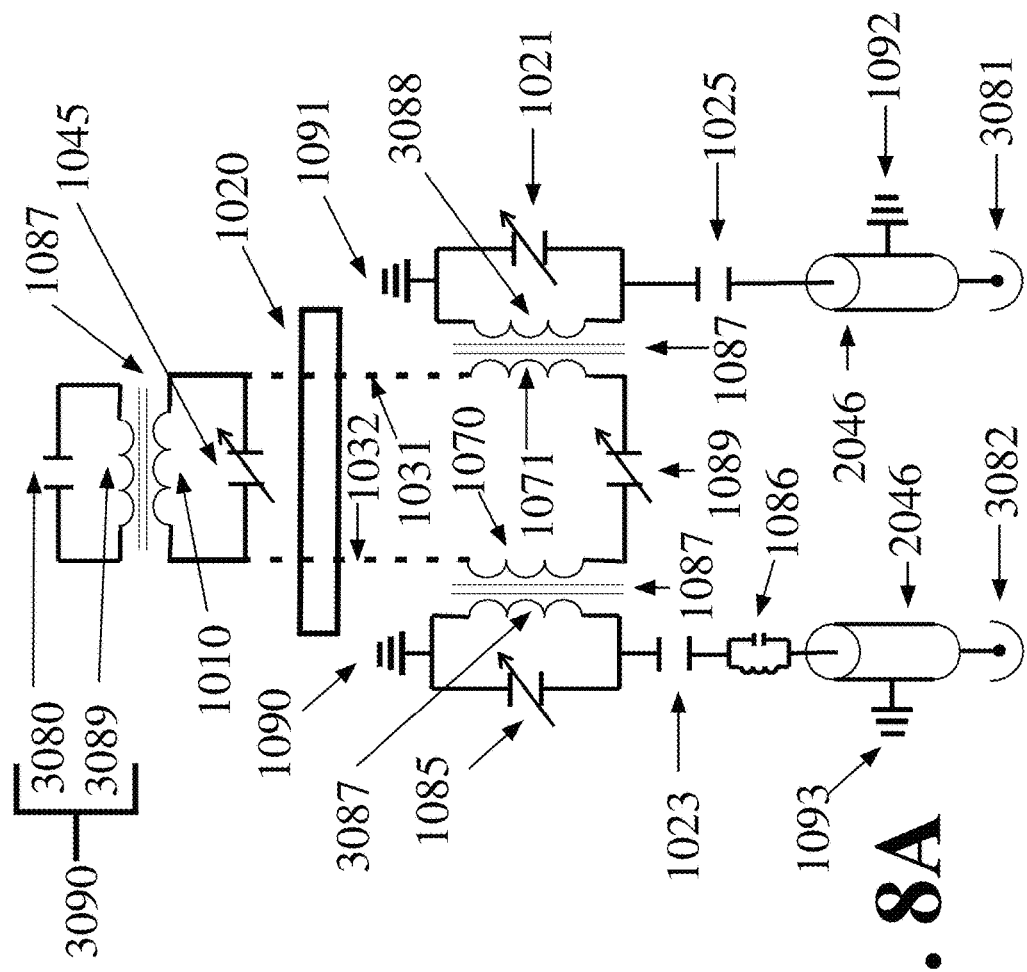
FIG. 8A is a schematic diagram showing a sample coil and resonator located above a lower insulator with the inductive coupling circuit(s) located below the lower insulator, according to an embodiment of the present invention.

FIG. 8A is a schematic diagram that is similar to FIG. 3A but with the addition of a resonator, 3090, that splits the primary resonance into two modes, $^1$H and 19F. Here the resonator, 3090, is coupled to the sample inductor via, 1087. In FIG. 8A the resonator, 3090, comprised of inductor, 3089, and capacitor, 3080, sample inductor, 1010, sample variable capacitor, 1045, which are located above a lower insulator, 1020, with the detection circuit(s) located below the lower insulator, according to an embodiment of the present invention. FIG. 8A shows a schematic diagram of a triple resonance circuit with a lower insulator 1020 for a split resonance circuit with inductive coupling to a sample inductor 1010 according to an embodiment of the invention. The sample inductor 1010 and a tune variable capacitor, 1045 are positioned above the lower insulator, 1020. Resonator lead #1 1031, and resonator lead #2, 1032 pass through the lower insulator, 1020 and connect the sample inductor, 1010 to inductor #1, 1070, and inductor #2, 1071. Below the lower insulator, 1020, inductor #1, 1070, inductively couples via 1087 to the coupling loop 3087. Here the match variable capacitor 1085 is used to match the circuit to 50 Ohms via the coupling capacitor 1023, the high frequency block, 1086, the 50 Ohm coax, 2046, and the $^2$H 50 Ohm port, 3082.

Inductor #2, 1071, couples via, 1087, to the coupling loop, 3088, where a match variable capacitor, 1021, is used to match the circuit to 50 Ohms via the coupling capacitor, 1025, fifty (50) Ohm coax, 2046, to the $^1$H (50) Ohm port, 3081. The variable capacitor, 1089, is used to tune the $^2$H resonance. Ground (#1), 1090, ground (#2), 1091, ground (#3), 1092, and ground (#4), 1093, are located in FIG. 8A. The ground points, 1090, 1091, 1092, 1093 associated with coupling loops, 3087, 3088 are not considered part of the resonant circuit since they do not contain high circulating current which is associated with resonant circuits. The circuit itself with the high circulating current has no ground points.

Figure 8B:
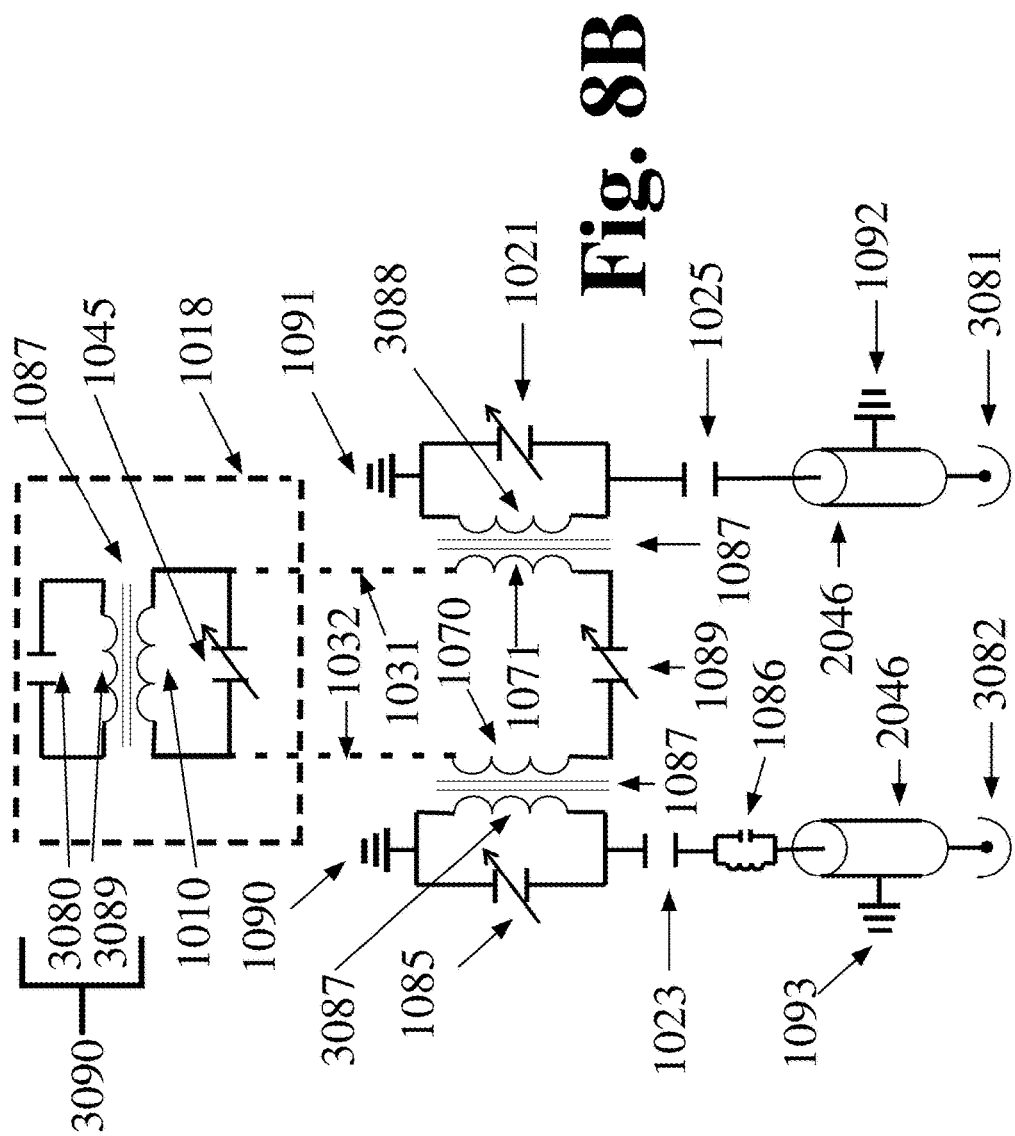
FIG. 8B is a schematic diagram showing a sample coil and resonator located in the sample coil region with the inductive coupling circuit(s) located outside the sample coil region in a manner similar to FIG. 8A, according to an embodiment of the present invention.

FIG. 8B is a schematic diagram that is similar to FIG. 3A but with the addition of a resonator, 3090, that splits the primary resonance into two modes, $^1$H and 19F. Here the resonator, 3090, is coupled to the sample inductor, 1010, via, 1087. In FIG. 8B the resonator, 3090, comprised of inductor, 3089, and capacitor, 3080, sample inductor, 1010, sample variable capacitor, 1045, which are located in the sample region, 1018, with the detection circuit(s) located distal to this region, according to an embodiment of the present invention. FIG. 8B shows a schematic diagram of a multiple resonance circuit with inductive coupling to a sample inductor 1010 according to an embodiment of the invention. The sample inductor 1010 and a tune variable capacitor, 1045 in sample region, 1018, are connected to resonator lead #1 1031, and resonator lead #2, 1032 pass through, 1018, and connect the sample inductor, 1010 to inductor #1, 1070, and inductor #2, 1071. Outside the region, 1018, inductor #1, 1070, inductively couples via 1087 to the coupling loop 3087. Here the match variable capacitor 1085 is used to match the circuit to 50 Ohms via the coupling capacitor 1023, the 50 Ohm coax, 2046, and the $^2$H 50 Ohm port, 3082. Inductor #2, 1071, couples via, 1087, to the coupling loop, 3088, where a match variable capacitor, 1021, is used to match the circuit to 50 Ohms via the coupling capacitor, 1025, fifty (50) Ohm coax, 2046, to the $^1$H (50) Ohm port, 3081. The variable capacitor, 1089, is used to tune the $^2$H resonance. Ground (#1), 1090, ground (#2), 1091, ground (#3), 1092, and ground (#4), 1093, are located in FIG. 8B. The ground points, 1090, 1091, 1092, 1093 associated with coupling loops, 3087, 3088 are not considered part of the resonant circuit since they do not contain high circulating current which is associated with resonant circuits. The circuit itself with the high circulating current has no ground points.

Figure 9A:
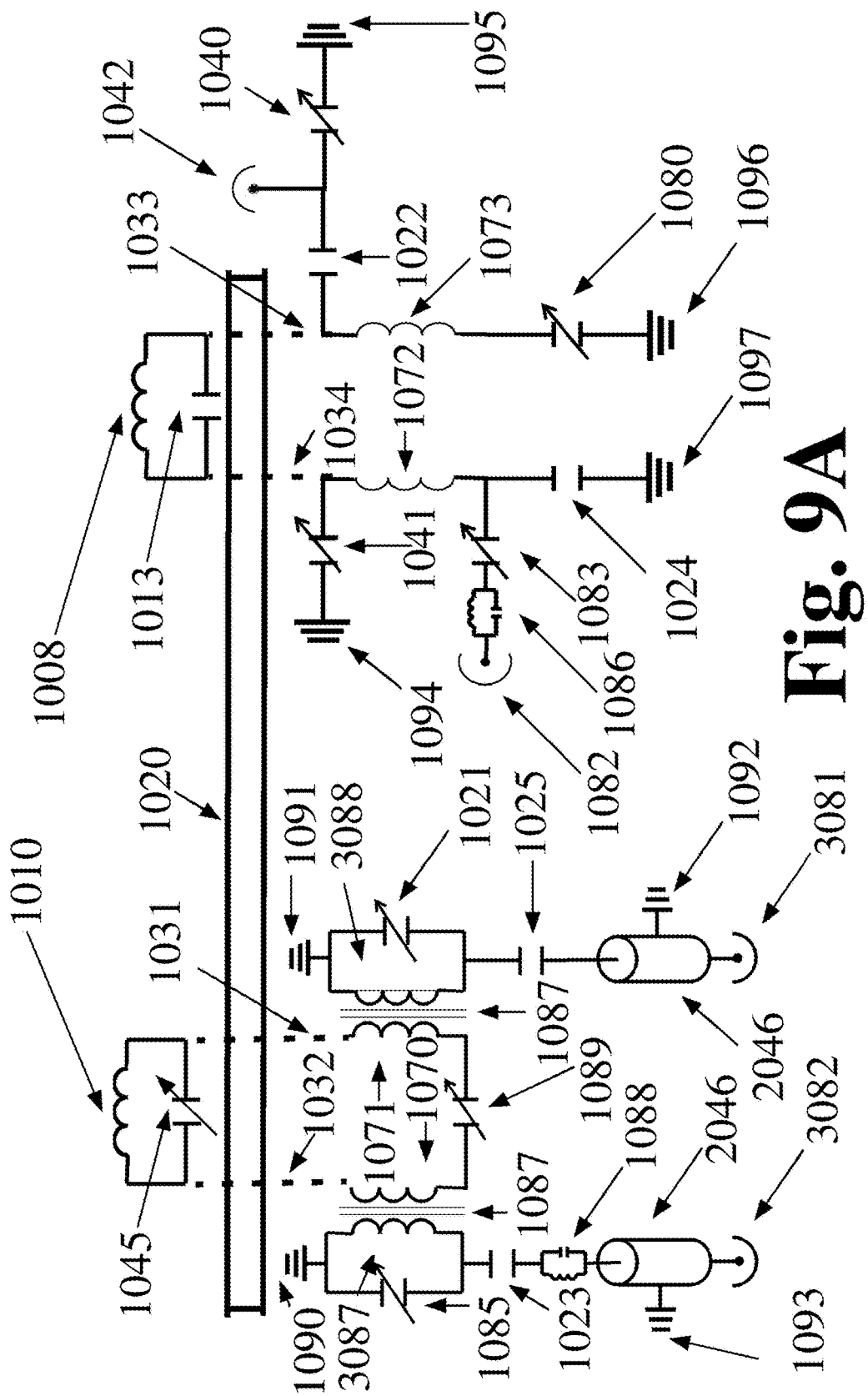
FIG. 9A is a schematic diagram showing a sample coil and a tertiary coil above a lower insulator and with inductive coupling circuit(s) located below the lower insulator, according to an embodiment of the present invention.

FIG. 9A is a schematic diagram of two coils, 1008 and 1010 (co-axial to each other with orthogonal magnetic fields) each with an associated inductor, 1008 and 1010 located above a lower insulator, 1020, according to an embodiment of the present invention. FIG. 9A consist of two double resonance circuits with a lower insulator, 1020. The circuit on the left is similar to FIG. 3A. The circuit on the right is similar to FIG. 1A. Above the lower insulator there are two sample coils, 1010, and, 1008 with 1010 being the tertiary coil. The circuit on the left shows a schematic diagram of a double resonance circuit with a lower insulator 1020 for a $^{13}$C/$^{15}$N double tuned circuit with inductive coupling to a sample inductor 1010 according to an embodiment of the invention. The sample inductor 1010 and a tune variable capacitor 1045 are positioned above the lower insulator 1020. Resonator lead #1 1031, and resonator lead #2, 1032 pass through the lower insulator, 1020 and connect the sample inductor, 1010 to the coupling inductor #1, 1070, and coupling inductor #2, 1071. Below the lower insulator, 1020, coupling inductor #1, 1070, inductively couples via 1087 to the coupling loop 3087. Here the match variable capacitor 1085 is used to match the circuit to 50 Ohms via the coupling capacitor 1023, the 50 Ohm coax, 2046, high frequency block, 1088, and the $^{15}$N 50 Ohm port, 3082. Coupling inductor #2, 1071, couples via, 1087, to the coupling loop, 3088, where a match variable capacitor, 1021, is used to match the circuit to 50 Ohms via the coupling capacitor, 1025, fifty (50) Ohm coax, 2046, to the $^{13}$C (50) Ohm port, 3081. The capacitor, 1045, is used to tune the $^{13}$C resonance. The capacitor, 1089, is used to tune the $^{15}$N resonance. Ground (#1), 1090, ground (#2), 1091, ground (#3), 1092, and ground (#4), 1093, are located in FIG. 9A. The ground points, 1090, 1091, 1092, 1093 associated with coupling loops, 3087, 3088 are not considered part of the resonant circuit since they do not contain high circulating current which is associated with resonant circuits. The circuit itself with the high circulating current has no ground points. The circuit on the right according to an embodiment of the invention shows a double tuned circuit for a $^1$H/$^2$H resonance, with a sample inductor, 1008, sample capacitor, 1013, positioned above the lower insulator, 1020. The resonator lead #1 1034, and resonator lead #2, 1033 pass through the lower insulator, 1020 and connect the sample inductor, 1010 to inductor #1, 1072, and inductor #2, 1073. In various embodiments of the invention, the length of the resonator lead #1, 1034, and resonator lead #2, 1073 are not necessarily the same. Below the lower insulator, 1020 are located a fixed tune capacitor, 1022, a tune variable capacitor, 1041, a match variable capacitor, 1040, a $^1$H fifty (50) Ohm port, 1042, a inductor #1, 1072, a inductor #2, 1073, a match variable capacitor, 1083, a tune variable capacitor, 1080, a high frequency block, 1086, a $^2$H fifty (50) Ohm port, 1082, a tune variable capacitor, 1080, ground (#1), 1090, ground (#2), 1091, ground (#3), 1092 and ground (#4) 1093. The high frequency block, 1086 comprises an inductor and a capacitor in parallel where the resonator blocks high frequencies. The choice of the high frequency block is made so as not to overlap with the primary resonance frequency.

Figure 9B:
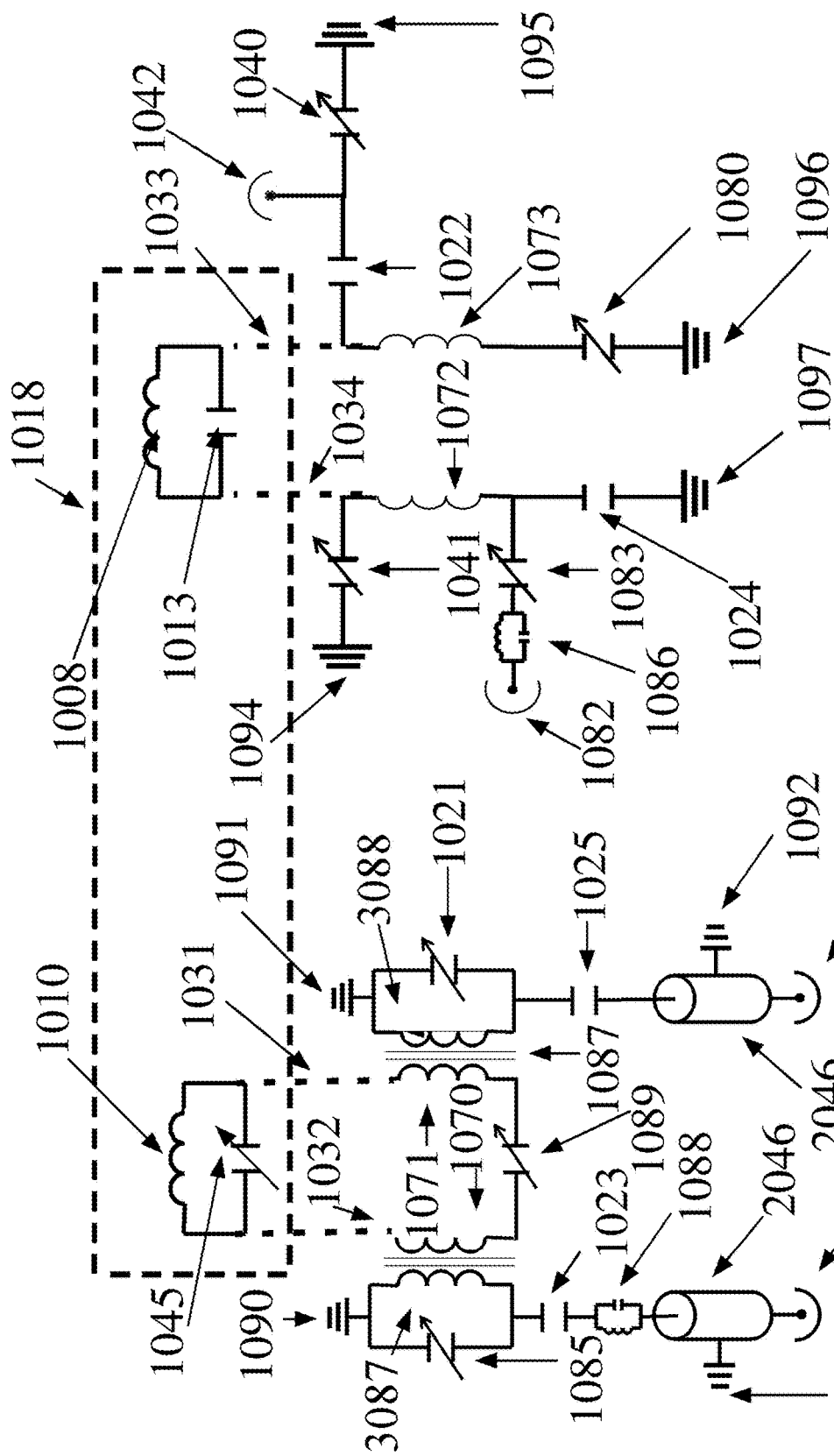
FIG. 9B is a schematic diagram showing a sample coil and a tertiary circuit located in the sample coil region and with the inductive coupling circuit(s) located outside the sample coil region, according to an embodiment of the present invention.

FIG. 9B shows a schematic diagram of two double resonance circuits emanating from a sample region, 1018. The circuit on the left is similar to FIG. 3A. The circuit on the right is similar to FIG. 1A. In the sample region there are two sample coils, 1010, and, 1008. These two sample coils are arranged coaxially with, 1010 being the tertiary coil. The circuit on the left shows a schematic diagram of a double resonance circuit distal to the sample region, 1018, for a $^{13}$C/$^{15}$N double tuned circuit with inductive coupling to a sample inductor 1010 according to an embodiment of the invention. The sample inductor 1010 and a tune variable capacitor, 1045 are positioned in the sample region, 1018. Resonator lead #1 1031, and resonator lead #2, 1032 pass through the sample region, 1018, and connect the sample inductor, 1010 to the coupling inductor #1, 1070, and coupling inductor #2, 1071. Distal to the sample region, 1018, coupling inductor #1, 1070, inductively couples via 1087 to the inductor coupling loop 3087. Here the variable capacitor 1085 is used to match the circuit to 50 Ohms via the coupling capacitor 1023, the 50 Ohm coax, 2046, the high frequency block, 1088, and the $^{15}$N 50 Ohm port, 3082. Coupling inductor #2, 1071, couples via, 1087, to the coupling loop, 3088, where a match variable capacitor, 1021, is used to match the circuit to 50 Ohms via the coupling capacitor, 1025, fifty (50) Ohm coax, 2046, to the $^{13}$C (50) Ohm port, 3081. The variable capacitor, 1089, is used to tune the 15N resonance. The variable capacitor, 1045, is use to tune the $^{13}$C resonance. Ground point (#1), 1090, ground point (#2), 1091, ground point (#3), 1092, and ground point (#4), 1093, are located in FIG. 9B. The ground points, #1, 1090, #2, 1091, #3, 1092, #4, 1093 associated with coupling loops, 3087, 3088 are not considered part of the resonant circuit since they do not contain high circulating current which is associated with resonant circuits. The circuit itself with the high circulating current has no ground points. The circuit on the right according to an embodiment of the invention shows a double tuned circuit for a $^1$H/$^2$H resonance, with a sample inductor, 1008, sample capacitor, 1013, positioned in the sample region, 1018. The resonator lead #1 1034, and resonator lead #2, 1073 pass through the region, 1018 and connect the sample inductor, 1008 to the coupling inductor #1, 1072, and coupling inductor #2, 1073. In various embodiments of the invention, the length of the resonator lead #1, 1034, and resonator lead #2, 1073 are not necessarily the same. Distal to the region, 1018 are located a $^1$H fixed tune capacitor, 1022, a tune variable capacitor, 1041, a match variable capacitor, 1040, a $^1$H fifty (50) Ohm port, 1042, inductor #1, 1072, inductor #2, 1073, a match variable capacitor, 1083, a tune variable capacitor, 1080, a high frequency block, 1086, a $^2$H fifty (50) Ohm port, 1082, a tune capacitor, 1080, ground (#5), 1094, ground (#6), 1095, ground (#7), 1096 and ground (#8) 1097. The high frequency block, 1086, comprises an inductor and a capacitor in parallel where the resonator blocks high frequencies. The choice of the high frequency block is made so as not to overlap with the primary resonance frequency.

Figure 10A:
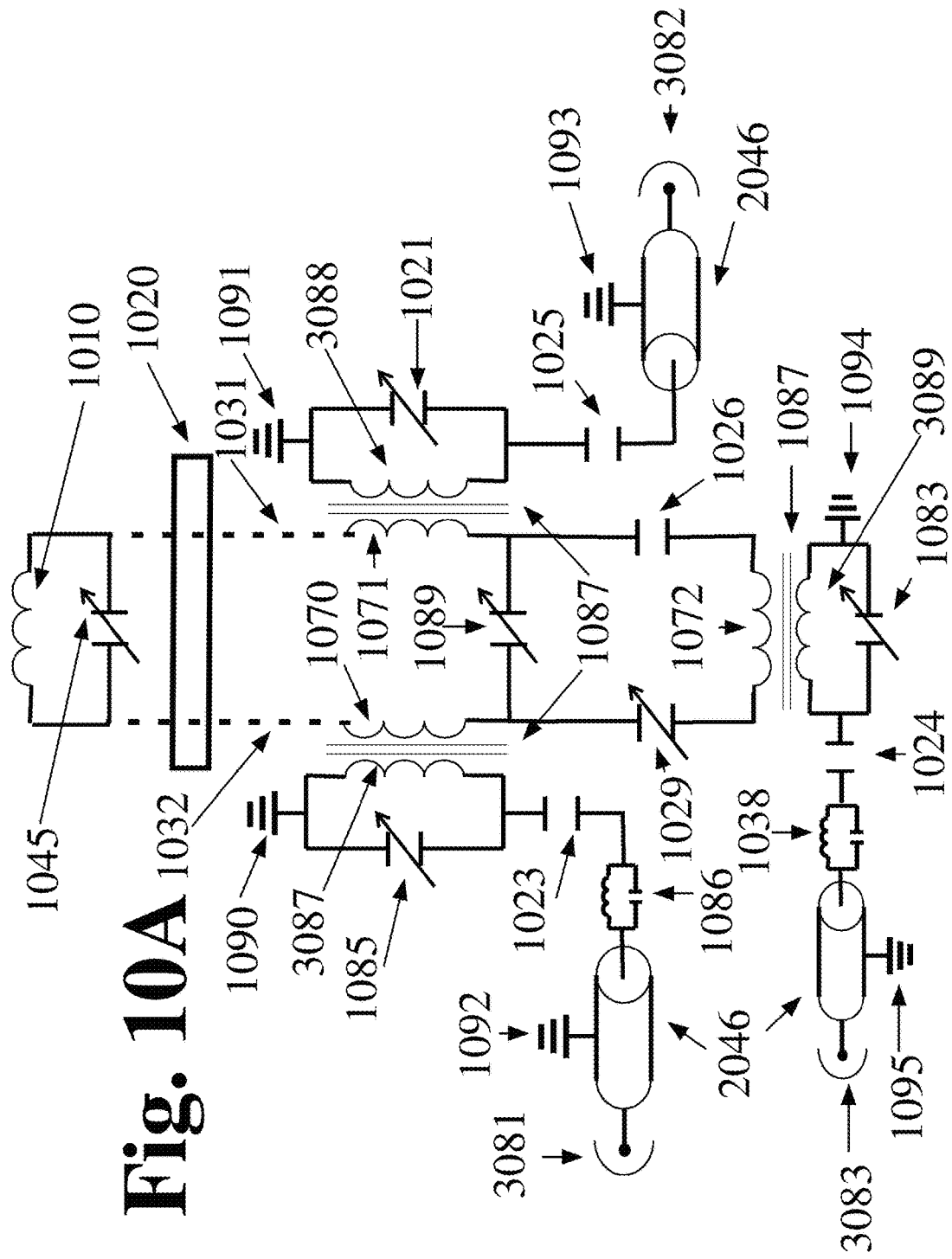
FIG. 10A is a schematic diagram showing a sample coil located above a lower insulator with the inductive coupling circuit(s) located below the lower insulator where the resonator splits the high frequency resonance into three modes, $^1H$, $^{13}C$ and $^{15}N$, according to an embodiment of the present invention.

FIG. 10A shows a schematic diagram of a triple resonance circuit with a lower insulator 1020 for a $^1$H/$^{13}$C/$^{15}$N circuit with inductive coupling to a sample inductor 1010 according to an embodiment of the invention. The sample inductor 1010 and a tune variable capacitor, 1045 are positioned above the lower insulator 1020. Resonator lead #1 1031, and resonator lead #2, 1032 pass through the lower insulator, 1020 and connect the sample inductor, 1010 to inductor #1, 1070, inductor #2, 1071 and inductor #3, 1072. Below the lower insulator, 1020, inductor #1, 1070, inductively couples via 1087 to the coupling loop 3087. Here the match variable capacitor, 1085, is used to match the circuit to 50 Ohms via the coupling capacitor 1023, a high frequency block, 1086, the 50 Ohm coax, 2046, and the 50 Ohm $^1$H port, 3081. For the high frequency ($^{13}$C) resonance, inductor #2, 1071, couples via, 1087, to the coupling loop, 3088, where a match variable capacitor, 1021, is used to match the circuit to 50 Ohms via the coupling capacitor, 1025, fifty (50) Ohm coax, 2046, to the $^{13}$C (50) Ohm port, 3082. Inductor #3, 1072, couples via, 1087, to the coupling loop, 3089, where a match variable capacitor, 1083, is used to match the circuit to 50 Ohms via the coupling capacitor, 1024, a high frequency block, 1038, fifty (50) Ohm coax, 2046, to the $^{15}$N fifty (50) Ohm port, 3083. Capacitor, 1089, is used to tune the $^1$H resonance. Capacitors 1026 and 1029 are used to tune the $^{15}$N resonance. Ground (#1), 1090, ground (#2), 1091, ground (#3), 1092, ground (#4), 1093, ground (#5), 1094, and ground (#6), 1095, are located in FIG. 10A. The ground points, 1090, 1091, 1092, 1093, 1094, 1095 associated with coupling loops, 3087, 3088 and 3089 are not considered part of the resonant circuit since they do not contain high circulating current which is associated with resonant circuits. The circuit itself with the high circulating current has no ground points.

Figure 10B:
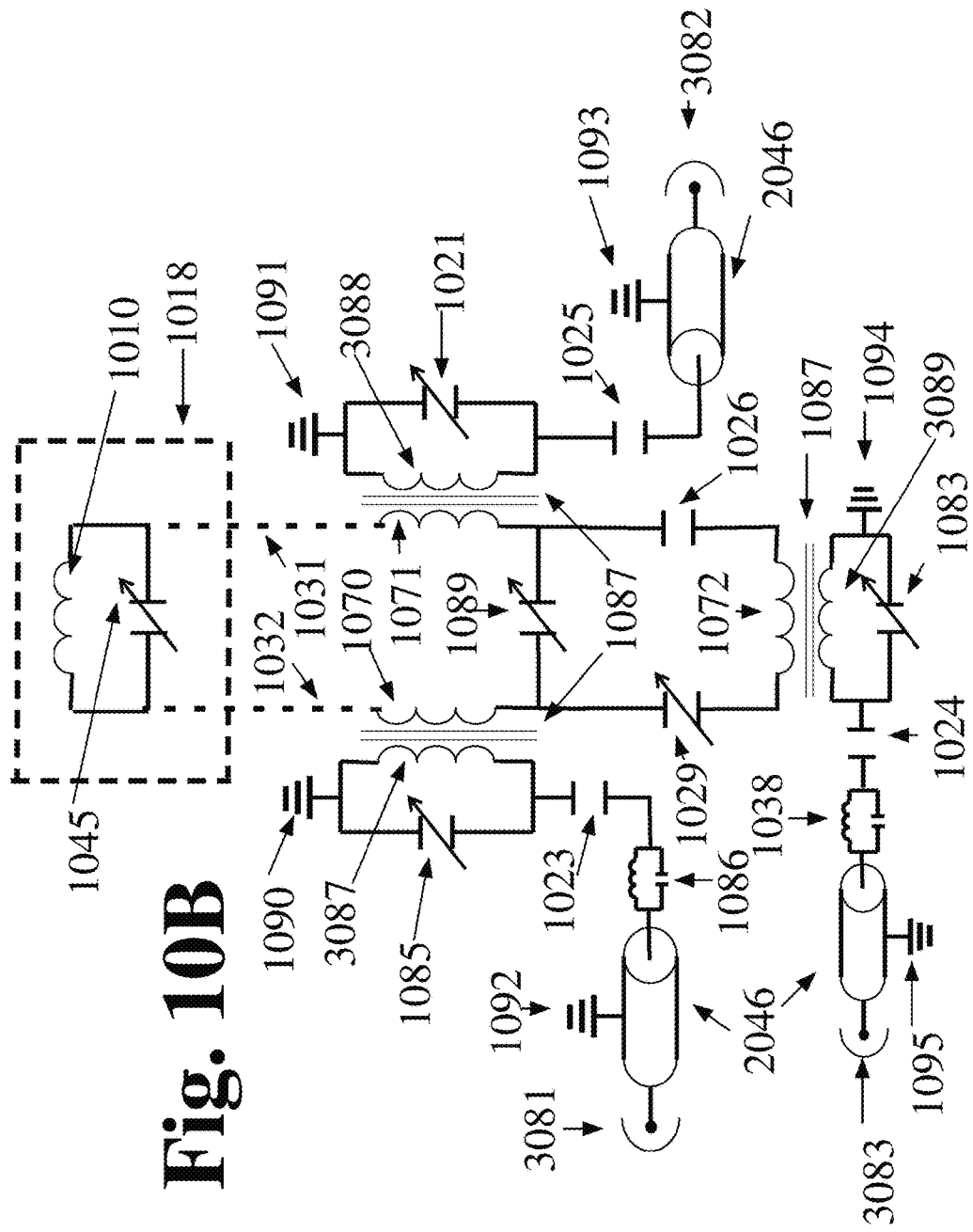
FIG. 10B is a schematic diagram showing a sample coil located in the sample resonator region with the inductive coupling circuit(s) located outside the sample resonator region in a manner similar to FIG. 10A, according to an embodiment of the present invention.

FIG. 10B shows a schematic diagram of a triple resonance circuit with a sample region, 1018, for a $^1$H/$^{13}$C/$^{15}$N circuit with inductive coupling to a sample inductor 1010 according to an embodiment of the invention. The sample inductor 1010 and a tune variable capacitor, 1045 are positioned in the sample region, 1018. Resonator lead #1 1031, and resonator lead #2, 1032 pass through the sample region, 1018 and connect the sample inductor, 1010 to inductor #1, 1070, inductor #2, 1071 and inductor #3, 1072. Distal to, 1018, inductor #1, 1070, inductively couples via 1087 to the coupling loop 3087. Here the match variable capacitor, 1085, is used to match the circuit to 50 Ohms via the coupling capacitor 1023, a high frequency block, 1086, the 50 Ohm coax, 2046, and the 50 Ohm $^1$H port, 3081. For the high frequency ($^{13}$C) resonance, inductor #2, 1071, couples via, 1087, to the coupling loop, 3088, where a match variable capacitor, 1021, is used to match the circuit to 50 Ohms via the coupling capacitor, 1025, fifty (50) Ohm coax, 2046, to the $^{13}$C (50) Ohm port, 3082. Inductor #3, 1072, couples via, 1087, to the coupling loop, 3089, where a match variable capacitor, 1083, is used to match the circuit to 50 Ohms via the coupling capacitor, 1024, a high frequency block, 1038, fifty (50) Ohm coax, 2046, to the $^{15}$N (50) Ohm port, 3083. Capacitor, 1089, is used to tune the $^1$H resonance. Capacitors 1026 and 1029 are used to tune the $^{15}$N resonance. Ground (#1), 1090, ground (#2), 1091, ground (#3), 1092, ground (#4), 1093, ground (#5), 1094, and ground (#6), 1095, are located in FIG. 10A. The ground points, 1090, 1091, 1092, 1093, 1094, 1095 associated with coupling loops, 3087, 3088 and 3089 are not considered part of the resonant circuit since they do not contain high circulating current which is associated with resonant circuits. The circuit itself with the high circulating current has no ground points. According to an alternative embodiment of the invention, a triple resonance circuit similar to that shown in FIG. 10A with a lower insulator 1020 or FIG. 10B without a lower insulator can be used for a $^{13}$C/$^2$H/$^{15}$N circuit with inductive coupling to a sample inductor 1010.

FIG. 10C is an S(1,1), S(2,2), S(3,3) plot which shows a linear circuit simulation which is carried out based on the simultaneous triple tune circuit shown in FIG. 10A according to an embodiment of the invention. The plot of signal intensity versus the frequency shows three peaks 10097, 10098 and 10099 with minimums for $^{15}$N at 50.48 MHz and −35.0 dB, 10097; for $^{13}$C at 125.7 MHz and −37.87 dB, 10098, and $^1$H at 500.1 MHz and −37.97 dB, 10099. In FIG. 10C, small 'trap' resonances are also observed, 10091, 10092 from the $^{15}$N signal and $^{13}$C signal respectively.

Because the RF homogeneity of solenoidal sample coils is easily perturbed, the proposed circuit arrangement using inductive coupling of secondary coils has important implications for the design of solid state NMR probes. Finally, the proposed circuit arrangement allows for 'no ground point' probe construction which in general helps maintain the CFF.

Nuclear magnetic resonance (NMR) signals are commonly detected with inductive radiofrequency (RF) pickup coils. All of these resonators can benefit from the ideas put forth by the ideas shown here regarding inductive coupling to these resonators.

In the following description, various aspects of the present invention are described. However, it will be apparent to those skilled in the art that the present invention can be practiced with only some or all aspects of the present invention. For purposes of explanation, specific numbers, materials, and configurations are set forth to provide a thorough understanding of the present invention. However, it will be apparent to one skilled in the art that the present invention can be practiced without the specific details. In other instances, well-known features are omitted or simplified in order not to obscure the present invention.

Parts of the description are presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) can take the form of electrical, magnetic, or optical signals capable of being stored, transferred, combined, and otherwise manipulated through electrical, optical, and/or biological components of a processor and its subsystems.

Various operations are described as multiple discrete steps in turn, in a manner that is helpful in understanding the present invention; however, the order of description should not be construed as to imply that these operations are necessarily order dependent.

Various embodiments are illustrated in terms of exemplary classes and/or objects in an object-oriented programming paradigm. It will be apparent to one skilled in the art that the present invention can be practiced using any number of different classes/objects, not merely those included here for illustrative purposes.

Aspects of the invention are illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

There remain encumbrances to the employment of inductively coupled probes to the NMR technique for a variety of samples and various experimental conditions. In general, dual probe circuits do not utilize inductive coupling to achieve the double-tuned circuit but rather use capacitive coupling to achieve the desired tuning properties. Here we show the use of inductive coupling to achieve the desired tuning properties.

The various modes in a circuit can be detected by matching the resistance in either the primary or the secondary (or any other) inductors. In an embodiment of the invention, it is advantageous to detect the modes preferentially in one inductor over another. There are a number of reasons why it is advantageous to detect the modes in a circuit by matching to the secondary coil rather than the primary coil.

Firstly, the parent coil might be sensitive to the presence of the detection coil.

Secondly, space considerations can determine that it is better to detect the signal in one spatial position versus another spatial position.

Thirdly, RF homogeneity can be affected by placing the detecting coil near the parent coil, whereas placing the detecting coil near the secondary coil may not alter the RF pattern of the parent coil.

Fourthly, it is possible to split the parent resonance mode into sub modes by inductive coupling to the secondary coil. An idler coil can be used to split the parent coil resonance into two modes. However, a double tuned $^1H/^2H$ circuit could have also been split ($^1H/^{19}F$) by placing the idler in close proximity to the secondary coil ($^2H$).

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, where the one or more resonators comprise an inductor and a capacitor in parallel.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, further comprising a resonator comprising an inductor and a capacitor in parallel located in the second region, where the resonator acts as a high frequency block, where the high frequency block does not overlap with the primary resonance mode.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, further comprising one or more components located in the first region selected from the group consisting of one or more coupling loops, one or more resonators and one or more tertiary circuits including one or more tertiary inductor coils.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, further comprising one or more components located in the first region selected from the group consisting of one or more coupling loops, one or more resonators and one or more tertiary circuits including one or more tertiary inductor coils, further comprising one or more supports located in the first region for supporting one or more of the primary inductor coil and the one or more components.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, further comprising one or more components located in the first region selected from the group consisting of one or more coupling loops, one or more resonators and one or more tertiary circuits including one or more tertiary inductor coils, further comprising an upper insulator, where the upper insulator insulates one or more of the primary inductor coil and the one or more components from one or both outside magnetic fields and outside electric fields.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, further comprising one or more components located in the first region selected from the group consisting of one or more coupling loops, one or more resonators and one or more tertiary circuits including one or more tertiary inductor coils, further comprising an upper insulator, where the upper insulator insulates one or more of the primary inductor coil and the one or more components from one or both outside magnetic fields and outside electric fields, further comprising a lower insulator, where the lower insulator separates the primary circuit and the one or more components from the one or more secondary circuits in the second region.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, where the distance is between a lower limit of approximately $10^{-4}$ m and an upper limit of approximately $10^{-1}$ m.

In an alternative embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, where the distance is between a lower limit of approximately $10^{-3}$ m and an upper limit of approximately $10^{-1}$ m.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, where the first region has a first volume between a lower limit of approximately $10^{-9}$ m$^3$ and an upper limit of approximately $10^{-1}$ m$^3$.

In an embodiment of the invention, a Nuclear Magnetic Resonance (NMR) probe comprises a primary circuit including a primary inductor coil with a primary resonance mode located in a first region of a NMR probe and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes, where the first region has a first volume between a lower limit of approximately $10^{-9}$ m$^3$ and an upper limit of approximately $10^{-1}$ m$^3$, where the second region has a second volume, where the ratio of the second volume to the first volume is between a lower limit of approximately $10^1$ and an upper limit of approximately $10^2$.

In an alternative embodiment of the invention, a Nuclear Magnetic Resonance probe comprises a primary circuit including a primary inductor coil with a primary resonance mode located in a first region, one or more secondary circuits including one or more secondary inductor coils located in a second region, where the second region is a distance from the first region between a lower limit of approximately $10^{-4}$ m and an upper limit of approximately $10^{-2}$ m, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes.

In an embodiment of the invention, a Nuclear Magnetic Resonance probe comprises a primary circuit including a primary inductor coil with a primary resonance mode located in a first region, one or more secondary circuits including one or more secondary inductor coils located in a second region a distance from the first region between a lower limit of approximately $10^{-4}$ m and an upper limit of approximately $10^{-2}$ m, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located in the second region inductively coupled to the one or more secondary inductor coils to detect one or more of the at least two modes.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or both one or more inductive coupling loops located in the second region inductively coupled to the one or more secondary inductor coils and one or more resonators located in the second region, where at least one of the one or more secondary inductor coils is coupled to the one or more resonators, where the one or more resonators split the primary resonance mode into at least two modes.

In an embodiment of the invention, a Nuclear Magnetic Resonance (NMR) probe comprises a primary circuit including a primary inductor coil with a primary resonance mode located in a first region, where the first region has a volume between a lower limit of approximately $10^{-9}$ m$^3$ and an upper limit of approximately $10^{-1}$ m$^3$, one or more secondary circuits including one or more secondary inductor coils located in a second region, where the second region is between a lower limit of approximately $10^{-4}$ m and an upper limit of approximately $10^{-1}$ m distance from the first region, where the one or more secondary inductor coils are electrically connected to the primary inductor coil and one or both one or more inductive coupling loops located in the second region inductively coupled to the one or more secondary inductor coils and one or more resonators located in the second region, where at least one of the one or more secondary inductor coils is coupled to the one or more resonators, where the one or more resonators split the primary resonance mode into at least two modes.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is a distance from the first region, where the first region has a first volume between a lower limit of approximately $10^{-9}$ m$^3$ and an upper limit of approximately $10^{-1}$ m$^3$, where the second region has a second volume, where the ratio of the second volume to the first volume is between a lower limit of approximately $10^1$ and an upper limit of approximately $10^2$, where the one or more secondary inductor coils are electrically connected to the primary inductor coil and one or both one or more inductive coupling loops located in the second region inductively coupled to the one or more secondary inductor coils and one or more resonators located in the second region, where at least one of the one or more secondary inductor coils is coupled to the one or more resonators, where the one or more resonators split the primary resonance mode into at least two modes.

In an embodiment of the invention, a Nuclear Magnetic Resonance (NMR) probe comprises a primary circuit including a primary inductor coil with a primary resonance mode located in a first region one or more secondary circuits including one or more secondary inductor coils located in a second region, where the one or more secondary circuits are between a lower limit of approximately $10^{-3}$ m and an upper limit of approximately $10^{-1}$ m from the first region, where the one or more secondary inductor coils are electrically connected to the primary inductor coil and one or both one or more inductive coupling loops located in the second region inductively coupled to the one or more secondary inductor coils and one or more resonators located in the second region, where at least one of the one or more secondary inductor coils is coupled to the one or more resonators, where the one or more resonators split the primary resonance mode into at least two modes.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils, further comprising one or more resonators located below the lower insulator, where at least one of the one or more secondary inductor coils is coupled to the one or more resonators, where the one or more resonators split the primary resonance mode into at least two mode, where the one or more resonators comprise an inductor and a capacitor in parallel.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils, further comprising a resonator including an inductor and a capacitor in parallel located below the lower insulator, where the resonator acts as a high frequency block, where the high frequency block does not overlap with the primary resonance mode.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils, further comprising one or more components located above the lower insulator selected from the group consisting of one or more coupling loops, one or more resonators and one or more tertiary circuits including one or more tertiary inductor coils.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils, further comprising one or more components located above the lower insulator selected from the group consisting of one or more coupling loops, one or more resonators and one or more tertiary circuits including one or more tertiary inductor coils, further comprising one or more supports located above the lower insulator for supporting one or more of the primary inductor coil and the one or more components.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils, further comprising one or more components located above the lower insulator selected from the group consisting of one or more coupling loops, one or more resonators and one or more tertiary circuits including one or more tertiary inductor coils, further comprising an upper insulator, where the upper insulator insulates one or more of the primary inductor coil and the one or more components from one or both outside magnetic fields and outside electric fields.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils, where the primary resonance mode is between a lower limit of approximately $3\times10^6$ Hz and an upper limit of approximately $3\times10^9$ Hz.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils, where the first region has a first volume between a lower limit of approximately $10^{-9}$ m$^3$ and an upper limit of approximately $10^{-1}$ m$^3$.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more inductive coupling loops located below the lower insulator inductively coupled to the one or more secondary inductor coils, where the first region has a first volume between a lower limit of approximately $10^{-9}$ m$^3$ and an upper limit of approximately $10^{-1}$ m$^3$, where the second region has a second volume, where the ratio of the second volume to the first volume is between a lower limit of approximately $10^1$ and an upper limit of approximately $10^2$.

In an alternative embodiment of the invention, a method of reducing a Nuclear Magnetic Resonance (NMR) probe volume comprises the steps of positioning a primary circuit including a primary inductor coil in a first volume of a NMR probe, where the primary inductor coil resonates at a primary resonance mode, positioning one or more secondary circuits including one or more secondary inductor coils outside the first volume, where the one or more secondary inductor coils is electrically connected to the primary inductor coil and positioning one or more resonators located outside the first volume, where at least one of the one or more secondary inductor coils is coupled to the one or more resonators, where the one or more resonators split the primary resonance mode into at least two modes.

In another embodiment of the invention, a kit for Nuclear Magnetic Resonance (NMR) measurement comprises a NMR probe including a primary circuit including a primary inductor coil located in a first region, where the primary inductor coil resonates at a primary resonance mode, one or more secondary circuits including one or more secondary inductor coils located in a second region a first distance between a lower limit of approximately $10^{-3}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes and instructions for adjusting the coupling constant of the one or more resonators to detect one or more of the at least two modes.

In an embodiment of the invention, a Nuclear Magnetic Resonance probe comprises a primary circuit including a primary inductor coil with a primary resonance mode located in a first region, one or more secondary circuits including one or more secondary inductor coils located in a second region, where the second region is a distance from the first region between a lower limit of approximately $10^{-4}$ m and an upper limit of approximately $10^{-2}$ m, where the one or more secondary inductor coils are electrically connected to the primary inductor coil and one or more inductive coupling loops located in the second region inductively coupled to the one or more secondary inductor coils.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more resonators located below the lower insulator, where at least one of the one or more secondary inductor coils is coupled to the one or more resonators, where the one or more resonators split the primary resonance mode into at least two modes.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more resonators located below the lower insulator, where at least one of the one or more secondary inductor coils is coupled to the one or more resonators, where the one or more resonators split the primary resonance mode into at least two modes, further comprising one or more inductive coupling loops located below the lower insulator inductively coupled to the one or more secondary inductor coils.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more resonators located below the lower insulator, where at least one of the one or more secondary inductor coils is coupled to the one or more resonators, where the one or more resonators split the primary resonance mode into at least two modes, further comprising a resonator including an inductor and a capacitor in parallel located below the lower insulator, where the resonator acts as a high frequency block, where the high frequency block does not overlap with the primary resonance mode.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more resonators located below the lower insulator, where at least one of the one or more secondary inductor coils is coupled to the one or more resonators, where the one or more resonators split the primary resonance mode into at least two modes, further comprising one or more components located above the lower insulator selected from the group consisting of one or more coupling loops, one or more resonators and one or more tertiary circuits including one or more tertiary inductor coils.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more resonators located below the lower insulator, where at least one of the one or more secondary inductor coils is coupled to the one or more resonators, where the one or more resonators split the primary resonance mode into at least two modes, further comprising one or more components located above the lower insulator selected from the group consisting of one or more coupling loops, one or more resonators and one or more tertiary circuits including one or more tertiary inductor coils, further comprising one or more supports located above the lower insulator for supporting one or more of the primary inductor coil and the one or more components.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more resonators located below the lower insulator, where at least one of the one or more secondary inductor coils is coupled to the one or more resonators, where the one or more resonators split the primary resonance mode into at least two modes, further comprising one or more components located above the lower insulator selected from the group consisting of one or more coupling loops, one or more resonators and one or more tertiary circuits including one or more tertiary inductor coils, further comprising an upper insulator, where the upper insulator insulates one or more of the primary inductor coil and the one or more components from one or both outside magnetic fields and outside electric fields.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more resonators located below the lower insulator, where at least one of the one or more secondary inductor coils is coupled to the one or more resonators, where the one or more resonators split the primary resonance mode into at least two modes, where the first region has a first volume between a lower limit of approximately $10^{-9}$ m$^3$ and an upper limit of approximately $10^{-1}$ m$^3$. In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil and one or more resonators located below the lower insulator, where at least one of the one or more secondary inductor coils is coupled to the one or more resonators, where the one or more resonators split the primary resonance mode into at least two modes, where the first region has a first volume between a lower limit of approximately $10^{-9}$ m$^3$ and an upper limit of approximately $10^{-1}$ m$^3$, where the second region has a second volume, where the ratio of the second volume to the first volume is between a lower limit of approximately $10^1$ and an upper limit of approximately $10^2$. In an alternative embodiment of the invention, a method of reducing a Nuclear Magnetic Resonance (NMR) probe volume comprising the steps of positioning a primary circuit including a primary inductor coil in a first volume of a NMR probe, where the primary inductor coil resonates at a primary resonance mode, positioning one or more secondary circuits including one or more secondary inductor coils outside the first volume, where the one or more secondary inductor coils is electrically connected to the primary inductor coil and positioning one or more inductive coupling loops located outside the first volume inductively coupled to the one or more secondary inductor coils, whereby positioning one or both the one or more secondary circuits and the one or more inductive coupling loops outside the first volume reduces a coupling constant of the circuit.

In an embodiment of the invention, a kit for Nuclear Magnetic Resonance (NMR) measurement comprises a NMR probe including a primary circuit including a primary inductor coil located in a first region, where the primary inductor coil resonates at a primary resonance mode, one or more secondary circuits including one or more secondary inductor coils located in a second region a first distance between a lower limit of approximately $10^{-3}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils and instructions for adjusting the one or more inductive coupling loops coupling constant (k) to detect the primary resonance mode.

In an embodiment of the invention, a kit for Nuclear Magnetic Resonance (NMR) measurement comprises a NMR probe including a primary circuit including a primary inductor coil located above a lower insulator, where the primary inductor coil resonates at a primary resonance mode, one or more secondary circuits including one or more secondary inductor coils located below the lower insulator, where the one or more secondary inductor coils are electrically connected to the primary inductor coil, and one or more resonators located below the lower insulator, where at least one of the one or more secondary inductor coils is coupled to the one or more resonators, where the one or more resonators split the primary resonance mode into at least two modes and instructions for adjusting the coupling constant of the one or more resonators to detect one or more of the at least two modes.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located below the lower insulator inductively coupled to the one or more secondary inductor coils to detect one or more of the at least two modes.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located below the lower insulator inductively coupled to the one or more secondary inductor coils to detect one or more of the at least two modes, further comprising a resonator including an inductor and a capacitor in parallel located below the lower insulator, where the resonator acts as a high frequency block, where the high frequency block does not overlap with the primary resonance mode.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located below the lower insulator inductively coupled to the one or more secondary inductor coils to detect one or more of the at least two modes, further comprising one or more components located above the lower insulator selected from the group consisting of one or more coupling loops, one or more resonators and one or more tertiary circuits including one or more tertiary inductor coils.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located below the lower insulator inductively coupled to the one or more secondary inductor coils to detect one or more of the at least two modes, further comprising one or more supports located above the lower insulator for supporting one or more of the primary inductor coil and the one or more components.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located below the lower insulator inductively coupled to the one or more secondary inductor coils to detect one or more of the at least two modes, further comprising an upper insulator, where the upper insulator insulates one or more of the primary inductor coil and the one or more components from one or both outside magnetic fields and outside electric fields.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located below the lower insulator inductively coupled to the one or more secondary inductor coils to detect one or more of the at least two modes, further comprising a lower insulator, where the lower insulator separates the primary circuit and the one or more components from the one or more secondary circuits.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located below the lower insulator inductively coupled to the one or more secondary inductor coils to detect one or more of the at least two modes, where the first region has a first volume between a lower limit of approximately $10^{-9}$ $m^3$ and an upper limit of approximately $10^{-1}$ $m^3$.

In an embodiment of the invention, a Nuclear Magnetic Resonance (NMR) probe comprises a primary circuit including a primary inductor coil located in a first region above a lower insulator with a primary resonance mode, one or more secondary circuits including one or more secondary inductor coils located in a second region below the lower insulator, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located below the lower insulator inductively coupled to the one or more secondary inductor coils to detect one or more of the at least two modes, where the first region has a first volume between a lower limit of approximately $10^{-9}$ $m^3$ and an upper limit of approximately $10^{-1}$ $m^3$, where the second region has a second volume, where the ratio of the second volume to the first volume is between a lower limit of approximately $10^1$ and an upper limit of approximately $10^2$.

In an alternative embodiment of the invention, a method of detecting coupling modes of a Nuclear Magnetic Resonance (NMR) signal comprising the steps of inductively coupling a NMR probe comprising a primary circuit including a primary inductor coil located above a lower insulator with a primary resonance mode, one or more secondary circuits including one or more secondary inductor coils located below the lower insulator, where the one or more secondary inductor coils are electrically connected to the primary inductor coil and one or both one or more inductive coupling loops located below the lower insulator inductively coupled to the one or more secondary inductor coils and one or more resonators located below the lower insulator, where at least one of the one or more secondary inductor coils is coupled to the one or more resonators, where the one or more resonators split the primary resonance mode into at least two modes and adjusting the one or more inductive coupling loops coupling constant (k) to detect one or more of the at least two modes.

In an embodiment of the invention, a kit for Nuclear Magnetic Resonance (NMR) measurement comprises a NMR probe including a primary circuit including a primary inductor coil located above a lower insulator, where the primary inductor coil resonates at a primary resonance mode one or more secondary circuits including one or more secondary inductor coils located below the lower insulator, where the one or more secondary inductor coils are electrically connected to the primary inductor coil and one or more inductive coupling loops located below the lower insulator inductively coupled to the one or more secondary inductor coils and instructions for adjusting the one or more inductive coupling loops coupling constant (k) to detect the primary resonance mode.

In an embodiment of the invention, a kit for Nuclear Magnetic Resonance (NMR) measurement comprises a NMR probe including a primary circuit including a primary inductor coil located above a lower insulator, where the primary inductor coil resonates at a primary resonance mode one or more secondary circuits including one or more secondary inductor coils located below the lower insulator, where the one or more secondary inductor coils are electrically connected to the primary inductor coil and one or more inductive coupling loops located below the lower insulator inductively coupled to the one or more secondary inductor coils and instructions for adjusting the one or more inductive coupling loops coupling constant (k) to detect the primary resonance mode, further comprising one or more resonators, where at least one of the one or more secondary inductor coils is coupled to the one or more resonators, where the one or more resonators split the primary resonance mode into at least two modes.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, further comprising one or more resonators located in the second region, where at least one of the one or more secondary inductor coils is coupled to the one or more resonators, where the one or more resonators split the primary resonance mode into at least two mode, where the one or more resonators comprise an inductor and a capacitor in parallel.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, further comprising a resonator including an inductor and a capacitor in parallel located in the second region, where the resonator acts as a high frequency block, where the high frequency block does not overlap with the primary resonance mode.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, further comprising one or more components located in the first region selected from the group consisting of one or more coupling loops, one or more resonators and one or more tertiary circuits including one or more tertiary inductor coils.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, further comprising one or more components located in the first region selected from the group consisting of one or more coupling loops, one or more resonators and one or more tertiary circuits including one or more tertiary inductor coils, further comprising one or more supports located in the first region for supporting one or more of the primary inductor coil and the one or more components.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, further comprising one or more components located in the first region selected from the group consisting of one or more coupling loops, one or more resonators and one or more tertiary circuits including one or more tertiary inductor coils, further comprising an upper insulator, where the upper insulator insulates one or more of the primary inductor coil and the one or more components from one or both outside magnetic fields and outside electric fields. In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, further comprising one or more components located in the first region selected from the group consisting of one or more coupling loops, one or more resonators and one or more tertiary circuits including one or more tertiary inductor coils, further comprising an upper insulator, where the upper insulator insulates one or more of the primary inductor coil and the one or more components from one or both outside magnetic fields and outside electric fields, further comprising a lower insulator, where the lower insulator separates the primary circuit and the one or more components from the one or more secondary circuits in the second region.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, where the first region has a first volume between a lower limit of approximately $10^{-9}$ m$^3$ and an upper limit of approximately $10^{-1}$ m$^3$.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, where the first region has a first volume between a lower limit of approximately $10^{-9}$ m$^3$ and an upper limit of approximately $10^{-1}$ m$^3$, where the second region has a second volume, where the ratio of the second volume to the first volume is between a lower limit of approximately $10^1$ and an upper limit of approximately $10^2$.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more inductive coupling loops located in the second region inductively coupled to the one or more secondary inductor coils, where the primary resonance mode is between a lower limit of approximately $3 \times 10^6$ Hz and an upper limit of approximately $3 \times 10^9$ Hz.

In an alternative embodiment of the invention, a method of minimizing RF inhomogeneity of a Nuclear Magnetic Resonance (NMR) signal comprising the steps of positioning a primary circuit including a primary inductor coil above a lower insulator in a first volume of a NMR probe, where the primary inductor coil resonates at a primary resonance mode and positioning one or more secondary circuits including one or more secondary inductor coils inductively coupled to one or more inductive coupling loops below a lower insulator, where the one or more secondary inductor coils are electrically connected to the primary inductor coil, whereby positioning the one or more inductive coupling loops minimizes RF inhomogeneity of the primary resonance mode.

In an alternative embodiment of the invention, a method of reducing a Nuclear Magnetic Resonance (NMR) probe volume comprising the steps of positioning a primary circuit including a primary inductor coil in a first volume of a NMR probe, where the primary inductor coil resonates at a primary resonance mode, positioning one or more secondary circuits including one or more secondary inductor coils outside the first volume, where the one or more secondary inductor coils is electrically connected to the primary inductor coil and positioning one or more resonators located outside the first volume, where at least one of the one or more secondary inductor coils is coupled to the one or more resonators, where the one or more resonators reduce a coupling constant of the primary circuit.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes, further comprising one or more inductive coupling loops located in the second region inductively coupled to the one or more secondary inductor coils.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes, further comprising a resonator including an inductor and a capacitor in parallel located in the second region, where the resonator acts as a high frequency block, where the high frequency block does not overlap with the primary resonance mode.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes, further comprising one or more components located in the first region selected from the group consisting of one or more coupling loops, one or more resonators and one or more tertiary circuits including one or more tertiary inductor coils.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes, further comprising one or more components located in the first region selected from the group consisting of one or more coupling loops, one or more resonators and one or more tertiary circuits including one or more tertiary inductor coils, further comprising one or more supports located in the first region for supporting one or more of the primary inductor coil and the one or more components.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes, further comprising one or more components located in the first region selected from the group consisting of one or more coupling loops, one or more resonators and one or more tertiary circuits including one or more tertiary inductor coils, further comprising an upper insulator, where the upper insulator insulates one or more of the primary inductor coil and the one or more components from one or both outside magnetic fields and outside electric fields.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes, further comprising one or more components located in the first region selected from the group consisting of one or more coupling loops, one or more resonators and one or more tertiary circuits including one or more tertiary inductor coils, further comprising an upper insulator, where the upper insulator insulates one or more of the primary inductor coil and the one or more components from one or both outside magnetic fields and outside electric fields, further comprising a lower insulator, where the lower insulator separates the primary circuit and the one or more components from the one or more secondary circuits in the second region.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes, where the first region has a first volume between a lower limit of approximately $10^{-9}$ m$^3$ and an upper limit of approximately $10^{-1}$ m$^3$.

In an embodiment of the invention, a Nuclear Magnetic Resonance (NMR) probe comprises a primary circuit including a primary inductor coil with a primary resonance mode located in a first region and one or more secondary circuits including one or more secondary inductor coils located in a second region, where the second region is between a lower limit of approximately $10^{-4}$ m and an upper limit of approximately $10^{-1}$ m from the first region, where the one or more secondary inductor coils are electrically connected to the primary inductor coil and one or more resonators located in the second region, where at least one of the one or more secondary inductor coils is coupled to the one or more resonators, where the one or more resonators split the primary resonance mode into at least two modes, where the first region has a first volume between a lower limit of approximately $10^{-9}$ m$^3$ and an upper limit of approximately $10^{-1}$ m$^3$, where the second region has a second volume, where the ratio of the second volume to the first volume is between a lower limit of approximately $10^1$ and an upper limit of approximately $10^2$.

In an embodiment of the invention, a method of detecting coupling modes of a Nuclear Magnetic Resonance (NMR) signal comprising the steps of inductively coupling the NMR probe comprising a primary circuit including a primary inductor coil with a primary resonance mode located in a first region and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes and adjusting the one or more inductive coupling loops coupling constant (k) to detect one or more of the at least two modes.

In an embodiment of the invention, a method of detecting coupling modes of a Nuclear Magnetic Resonance (NMR) signal comprising the steps of inductively coupling the NMR probe comprising a primary circuit including a primary inductor coil with a primary resonance mode located in a first region and one or more secondary circuits located in a second region where the second region is a distance from the first region including: one or more secondary inductor coils, where the one or more secondary inductor coils are electrically connected to the primary inductor coil and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes and adjusting the one or more inductive coupling loops coupling constant (k) to detect one or more of the at least two modes, further comprising adjusting the coupling constant with one or more shunts.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region between a lower limit of approximately $10^{-4}$ m and an upper limit of approximately $10^{-1}$ m distant from the first region, where the volume of the first region is between a lower limit of approximately $10^{-9}$ m$^3$ and an upper limit of approximately $10^{-1}$ m$^3$; where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located in the second region inductively coupled to the one or more secondary inductor coils to detect one or more of the at least two modes.

In an embodiment of the invention, a Nuclear Magnetic Resonance (NMR) probe comprises a primary circuit including a primary inductor coil with a primary resonance mode located in a first region, one or more secondary circuits including one or more secondary inductor coils located in a second region between a lower limit of approximately $10^{-4}$ m and an upper limit of approximately $10^{-1}$ m distant from the first region, where the volume of the first region is between a lower limit of approximately $10^{-9}$ m$^3$ and an upper limit of approximately $10^{-1}$ m$^3$; where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located in the second region inductively coupled to the one or more secondary inductor coils to detect one or more of the at least two modes, where the volume of the second region is between a lower limit of approximately $10^1$ and an upper limit of approximately $10^2$ times the volume of the first region.

In an embodiment of the invention, a method of reducing a Nuclear Magnetic Resonance (NMR) probe volume comprises the steps of positioning a primary circuit including a primary inductor coil in a first volume of a NMR probe, where the primary inductor coil resonates at a primary resonance mode, positioning one or more secondary circuits including one or more secondary inductor coils outside the first volume, where the one or more secondary inductor coils is electrically connected to the primary inductor coil and positioning one or more inductive coupling loops located outside the first volume inductively coupled to the one or more secondary inductor coils, whereby positioning one or both the one or more secondary circuits and the one or more inductive coupling loops outside the first volume reduces the first volume.

In an embodiment of the invention, a method of reducing a Nuclear Magnetic Resonance (NMR) probe volume comprises the steps of positioning a primary circuit including a primary inductor coil in a first volume of a NMR probe, where the primary inductor coil resonates at a primary resonance mode, positioning one or more secondary circuits including one or more secondary inductor coils outside the first volume, where the one or more secondary inductor coils is electrically connected to the primary inductor coil and positioning one or more inductive coupling loops located outside the first volume inductively coupled to the one or more secondary inductor coils, whereby positioning one or both the one or more secondary circuits and the one or more inductive coupling loops outside the first volume reduces the first volume, further comprising one or more resonators, where at least one of the one or more secondary inductor coils is coupled to the one or more resonators, where the one or more resonators split the primary resonance mode into at least two modes.

In an embodiment of the invention, a method of reducing a Nuclear Magnetic Resonance (NMR) probe volume comprises the steps of positioning a primary circuit including a primary inductor coil in a first volume of a NMR probe, where the primary inductor coil resonates at a primary resonance mode, positioning one or more secondary circuits including one or more secondary inductor coils outside the first volume, where the one or more secondary inductor coils is electrically connected to the primary inductor coil and positioning one or more inductive coupling loops located outside the first volume inductively coupled to the one or more secondary inductor coils, whereby positioning one or both the one or more secondary circuits and the one or more inductive coupling loops outside the first volume reduces the first volume, further comprising adjusting the resistance of the one or mode inductive coupling loops to fifty (50) ohm coax.

In an embodiment of the invention, a method of reducing a Nuclear Magnetic Resonance (NMR) probe volume comprises the steps of positioning a primary circuit including a primary inductor coil in a first volume of a NMR probe, where the primary inductor coil resonates at a primary resonance mode, positioning one or more secondary circuits including one or more secondary inductor coils outside the first volume, where the one or more secondary inductor coils is electrically connected to the primary inductor coil and positioning one or more inductive coupling loops located outside the first volume inductively coupled to the one or more secondary inductor coils, whereby positioning one or both the one or more secondary circuits and the one or more inductive coupling loops outside the first volume reduces the first volume, further comprising positioning one or more tertiary circuits including one or more tertiary inductor coils in the first region.

In an embodiment of the invention, a method of reducing a Nuclear Magnetic Resonance (NMR) probe sample coil volume comprises the steps of positioning a primary circuit comprising a primary inductor coil and a capacitor in a first volume of a NMR probe, where the primary inductor coil resonates at a primary resonance mode and positioning one or more secondary circuits including one or more secondary inductor coils a first distance from the first volume, where the one or more secondary inductor coils are electrically connected to the primary inductor coil, where at least one of the one or more secondary inductor coils is coupled to one or more resonators, where the one or more resonators split the primary resonance mode into at least two modes, whereby positioning one or both the one or more secondary circuits and the one or more secondary inductor coils outside the first volume reduces the first volume.

In an embodiment of the invention, a method of reducing a Nuclear Magnetic Resonance (NMR) probe sample coil volume comprises the steps of positioning a primary circuit comprising a primary inductor coil and a capacitor in a first volume of a NMR probe, where the primary inductor coil resonates at a primary resonance mode and positioning one or more secondary circuits including one or more secondary inductor coils a first distance from the first volume, where the one or more secondary inductor coils are electrically connected to the primary inductor coil, where at least one of the one or more secondary inductor coils is coupled to one or more resonators, where the one or more resonators split the primary resonance mode into at least two modes, whereby positioning one or both the one or more secondary circuits and the one or more secondary inductor coils outside the first volume reduces the first volume, further comprising positioning one or more inductive coupling loops inductively coupled to the one or more secondary inductor coils outside the first volume.

In an embodiment of the invention, a method of reducing a Nuclear Magnetic Resonance (NMR) probe sample coil volume comprises the steps of positioning a primary circuit comprising a primary inductor coil and a capacitor in a first volume of a NMR probe, where the primary inductor coil resonates at a primary resonance mode and positioning one or more secondary circuits including one or more secondary inductor coils a first distance from the first volume, where the one or more secondary inductor coils are electrically connected to the primary inductor coil, where at least one of the one or more secondary inductor coils is coupled to one or more resonators, where the one or more resonators split the primary resonance mode into at least two modes, whereby positioning one or both the one or more secondary circuits and the one or more secondary inductor coils outside the first volume reduces the first volume, further comprising positioning one or more inductive coupling loops inductively coupled to the one or more secondary inductor coils outside the first volume, where a resistance of the one or more inductive coupling loops is adjusted to fifty (50) ohm coax.

In an embodiment of the invention, a method of reducing a Nuclear Magnetic Resonance (NMR) probe sample coil volume comprises the steps of positioning a primary circuit comprising a primary inductor coil and a capacitor in a first volume of a NMR probe, where the primary inductor coil resonates at a primary resonance mode and positioning one or more secondary circuits including one or more secondary inductor coils a first distance from the first volume, where the one or more secondary inductor coils are electrically connected to the primary inductor coil, where at least one of the one or more secondary inductor coils is coupled to one or more resonators, where the one or more resonators split the primary resonance mode into at least two modes, whereby positioning one or both the one or more secondary circuits and the one or more secondary inductor coils outside the first volume reduces the first volume, where the first distance is between a lower limit of approximately $10^{-4}$ m and an upper limit of approximately $10^{-2}$ m.

In an embodiment of the invention, a method of reducing a Nuclear Magnetic Resonance (NMR) probe sample coil volume comprises the steps of positioning a primary circuit comprising a primary inductor coil and a capacitor in a first volume of a NMR probe, where the primary inductor coil resonates at a primary resonance mode and positioning one or more secondary circuits including one or more secondary inductor coils a first distance from the first volume, where the one or more secondary inductor coils are electrically connected to the primary inductor coil, where at least one of the one or more secondary inductor coils is coupled to one or more resonators, where the one or more resonators split the primary resonance mode into at least two modes, whereby positioning one or both the one or more secondary circuits and the one or more secondary inductor coils outside the first volume reduces the first volume, where the first volume is between a lower limit of approximately $10^{-9}$ m$^3$ and an upper limit of approximately $10^{-1}$ m$^3$.

In an alternative embodiment of the invention, a method of minimizing RF inhomogeneity of a Nuclear Magnetic Resonance (NMR) signal comprising the steps of positioning a primary circuit including a primary inductor coil in a first volume of a NMR probe, where the primary inductor coil resonates at a primary resonance mode and positioning one or more secondary circuits including one or more secondary inductor coils inductively coupled to one or more inductive coupling loops a first distance outside the first volume, where the one or more secondary inductor coils are electrically connected to the primary inductor coil, whereby positioning the one or more inductive coupling loops minimizes RF inhomogeneity of the primary resonance mode.

In an embodiment of the invention, a method of minimizing RF inhomogeneity of a Nuclear Magnetic Resonance (NMR) signal comprising the steps of positioning a primary circuit including a primary inductor coil in a first volume of a NMR probe, where the primary inductor coil resonates at a primary resonance mode and positioning one or more secondary circuits including one or more secondary inductor coils inductively coupled to one or more inductive coupling loops a first distance outside the first volume, where the one or more secondary inductor coils are electrically connected to the primary inductor coil, whereby positioning the one or more inductive coupling loops minimizes RF inhomogeneity of the primary resonance mode, further comprising where at least one of the one or more secondary inductor coils is coupled to one or more resonators, where the one or more resonators split the primary resonance mode into at least two modes.

In an embodiment of the invention, a method of minimizing RF inhomogeneity of a Nuclear Magnetic Resonance (NMR) signal comprising the steps of positioning a primary circuit including a primary inductor coil in a first volume of a NMR probe, where the primary inductor coil resonates at a primary resonance mode and positioning one or more secondary circuits including one or more secondary inductor coils inductively coupled to one or more inductive coupling loops a first distance outside the first volume, where the one or more secondary inductor coils are electrically connected to the primary inductor coil, whereby positioning the one or more inductive coupling loops minimizes RF inhomogeneity of the primary resonance mode, further comprising adjusting a resonator including an inductor and a capacitor in parallel, where the resonator acts as a high frequency block, where the high frequency block does not overlap with a resonance frequency of the primary inductor coil.

In an embodiment of the invention, a method of minimizing RF inhomogeneity of a Nuclear Magnetic Resonance (NMR) signal comprising the steps of positioning a primary circuit including a primary inductor coil in a first volume of a NMR probe, where the primary inductor coil resonates at a primary resonance mode and positioning one or more secondary circuits including one or more secondary inductor coils inductively coupled to one or more inductive coupling loops a first distance outside the first volume, where the one or more secondary inductor coils are electrically connected to the primary inductor coil, whereby positioning the one or more inductive coupling loops minimizes RF inhomogeneity of the primary resonance mode, where the first distance is between a lower limit of approximately $10^{-4}$ m and an upper limit of approximately $10^{-2}$ m.

In an embodiment of the invention, a method of minimizing RF inhomogeneity of a Nuclear Magnetic Resonance (NMR) signal comprising the steps of positioning a primary circuit including a primary inductor coil in a first volume of a NMR probe, where the primary inductor coil resonates at a primary resonance mode and positioning one or more secondary circuits including one or more secondary inductor coils inductively coupled to one or more inductive coupling loops a first distance outside the first volume, where the one or more secondary inductor coils are electrically connected to the primary inductor coil, whereby positioning the one or more inductive coupling loops minimizes RF inhomogeneity of the primary resonance mode, further comprising adjusting the first volume to between a lower limit of approximately $10^{-9}$ m$^3$ and an upper limit of approximately $10^{-3}$ m$^3$.

In an embodiment of the invention, a nuclear magnetic resonance probe comprises a primary circuit including a primary inductor coil with a primary resonance mode located in a first region, one or more secondary circuits including one or more secondary inductor coils located in a second region a distance from the first region between a lower limit of approximately $10^{-4}$ m and an upper limit of approximately $10^{-2}$ m, where the one or more secondary inductor coils are electrically connected to the primary inductor coil, where at least one of the one or more secondary inductor coils is coupled to one or more resonators, where the one or more resonators split the primary resonance mode into at least two modes and one or more inductive coupling loops located in the second region inductively coupled to the one or more secondary inductor coils to detect the at least two modes.

The above concepts have use in the construction of both liquid and solid sample NMR probes. It may also have application to Magnetic resonance circuitry as used in Electron Spin Resonance, Magnetic Resonance Imaging, Geological studies, including oil well logging, and Magnetic Resonance Imaging medical devices. A person of ordinary skill in the art would understand how to modify these uses of magnetic resonance with the teachings of the present invention.

While the systems, methods, and devices have been illustrated by the described examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and devices provided herein. Additional advantages and modifications will readily be apparent to those skilled in the art. Therefore, the invention, in its broader aspects, is not limited to the specific details, the representative system, method or device, and illustrative examples shown and described. Accordingly, departures may be made from such details without departing from the spirit or scope of the applicant's general inventive concept. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents. In any multiply tuned circuit you have at least as many modes as you have inductors.

The invention claimed is:

1. A Nuclear Magnetic Resonance probe comprising:
a primary circuit including a primary inductor coil with a primary resonance mode located in a first region;
one or more secondary circuits including one or more secondary inductor coils located in a second region a distance from the first region between:
a lower limit of approximately $10^{-4}$ m; and
an upper limit of approximately $10^{-2}$ m;
where the one or more secondary inductor coils are electrically connected to the primary inductor coil, where at least one of the one or more secondary inductor coils is coupled to one or more resonators, where the one or more resonators split the primary resonance mode into at least two modes; and
one or more inductive coupling loops located in the second region inductively coupled to the one or more secondary inductor coils to detect one or more of the at least two modes.

2. The NMR probe of claim 1, where the one or more resonators comprise an inductor and a capacitor in parallel.

3. The NMR probe of claim 1, further comprising a resonator comprising an inductor and a capacitor in parallel located in the second region, where the resonator acts as a high frequency block, where the high frequency block does not overlap with the primary resonance mode.

4. The NMR probe of claim 1, further comprising one or more components located in the first region selected from the group consisting of one or more coupling loops, one or more resonators and one or more tertiary circuits including one or more tertiary inductor coils.

5. The NMR probe of claim 4, further comprising one or more supports located in the first region for supporting one or more of the primary inductor coil and the one or more components.

6. The NMR probe of claim 4, further comprising an upper insulator, where the upper insulator insulates one or both the primary inductor coil and the one or more components from one or both outside magnetic fields and outside electric fields.

7. The NMR probe of claim 6, further comprising a lower insulator, where the lower insulator separates the primary circuit and the one or more components from the one or more secondary circuits in the second region.

8. The NMR probe of claim 1, where the distance is between:
a lower limit of approximately $10^{-4}$ m; and
an upper limit of approximately $10^{-1}$ m.

9. The NMR probe of claim 1, where the first region has a first volume between:
a lower limit of approximately $10^{-9}$ m$^3$; and
an upper limit of approximately $10^{-1}$ m$^3$.

10. The NMR probe of claim 9, where the second region has a second volume, where the ratio of the second volume to the first volume is between:
a lower limit of approximately $10^1$; and
an upper limit of approximately $10^2$.

11. The NMR probe of claim 1, where the primary resonance mode is between:
a lower limit of approximately $3\times10^6$ Hz; and
an upper limit of approximately $3\times10^9$ Hz.

12. A Nuclear Magnetic Resonance (NMR) probe comprising:
a primary circuit including a primary inductor coil with a primary resonance mode located in a first region;
one or more secondary circuits including one or more secondary inductor coils located in a second region, where the one or more secondary circuits are between:
a lower limit of approximately $10^{-3}$ m; and
an upper limit of approximately $10^{-1}$ m from the first region,
where the one or more secondary inductor coils are electrically connected to the primary inductor coil; and
one or both one or more inductive coupling loops located in the second region inductively coupled to the one or more secondary inductor coils and one or more resonators located in the second region, where at least one of the one or more secondary inductor coils is coupled to the one or more resonators, where the one or more resonators split the primary resonance mode into at least two modes.

13. The NMR probe of claim 12, where the one or more resonators comprise an inductor and a capacitor in parallel.

14. The NMR probe of claim 12, further comprising a resonator comprising an inductor and a capacitor in parallel located in the second region, where the resonator acts as a high frequency block, where the high frequency block does not overlap with the primary resonance mode.

15. The NMR probe of claim 12, further comprising one or more components located in the first region selected from the group consisting of one or more coupling loops, one or more resonators and one or more tertiary circuits including one or more tertiary inductor coils.

16. A method of detecting coupling modes of a Nuclear Magnetic Resonance (NMR) signal comprising the steps of:
   (A) inductively coupling the NMR probe comprising:
   a primary circuit including a primary inductor coil with a primary resonance mode located in a first region; and one or more secondary circuits located in a second region where the second region is a distance from the first region including: one or more secondary inductor coils, where the one or more secondary inductor coils are electrically connected to the primary inductor coil; and one or both one or more inductive coupling loops inductively coupled to the one or more secondary inductor coils and one or more resonators, where at least one of the one or more secondary inductor coils is coupled to the one or more resonators, where the one or more resonators split the primary resonance mode into at least two modes; and (B) adjusting the one or more inductive coupling loops coupling constant (k) to detect one or more of the at least two modes.

17. The method of claim 16, further comprising adjusting the coupling constant with one or more shunts.

* * * * *